(12) United States Patent
Satou et al.

(10) Patent No.: US 7,243,031 B2
(45) Date of Patent: Jul. 10, 2007

(54) METHOD OF DESIGNING MULTIFUNCTIONAL BASE SEQUENCE

(75) Inventors: Yoko Satou, Fukuoka (JP); Masato Kitajima, Fukuoka (JP); Kiyotaka Shiba, Tokyo (JP)

(73) Assignees: Fujitsu Limited, Kawasaki (JP); Kiyotaka Shiba, Tokyo (JP)

( * ) Notice: Subject to any disclaimer, the term of this patent is extended or adjusted under 35 U.S.C. 154(b) by 438 days.

(21) Appl. No.: 10/746,036

(22) Filed: Dec. 29, 2003

(65) Prior Publication Data

US 2004/0214206 A1  Oct. 28, 2004

Related U.S. Application Data

(63) Continuation-in-part of application No. 10/329,781, filed on Dec. 27, 2002, now abandoned.

(30) Foreign Application Priority Data

Dec. 27, 2001 (JP) ............... 2001-397390
Dec. 27, 2002 (JP) ............... 2002-380360

(51) Int. Cl.
*G06F 19/00* (2006.01)
*C12N 15/11* (2006.01)
*C07K 14/00* (2006.01)

(52) U.S. Cl. ............... 702/20; 536/23.1; 530/300
(58) Field of Classification Search ............... None
See application file for complete search history.

(56) References Cited

U.S. PATENT DOCUMENTS 6,063,595 A     5/2000  Shiba
2003/0121065 A1 * 6/2003  Shiba ............... 800/8

FOREIGN PATENT DOCUMENTS

JP   9-154585      6/1997
JP   9-322775     12/1997
JP   2001-352990  12/2001
WO   WO 01/96558 * 12/2001

OTHER PUBLICATIONS

Shiba et al., "Creation of Libraries with Long ORF's by Polymerization of a Microgene", Proc. Natl. Acad. Sci. USA, vol. 94, pp. 3805-3810, Apr. 1997.

* cited by examiner

*Primary Examiner*—John S. Brusca
(74) *Attorney, Agent, or Firm*—Staas & Halsey LLP

(57) ABSTRACT

A multifunctional base sequence method largely shortens the calculation time and reduces the volume of memory consumption of a processor by carrying out calculation with the advance exclusion of base sequences in which translation termination codons emerge in the second and third reading frames, which are to be excluded in the end. Focusing on the fact that a dipeptide sequence already contains information about the translation products of the second and third reading frames, proteins are analyzed and calculated as duplicated connective products of dipeptide sequences, and are not analyzed as connective products of 20 kinds of amino acids.

20 Claims, 15 Drawing Sheets

FIG. 1

| Leu | | Ser | | Leu Ser | |
|---|---|---|---|---|---|
| TTA | | TCT | | TTA TCT | CTC TCT |
| TTG | | TCC | | TTA TCC | CTC TCC |
| CTT | × | TCA | = | TTA TCA | CTC TCA |
| CTC | | TCG | | TTA TCG | CTC TCG |
| CTA | | AGT | | TTA AGT | CTC AGT |
| CTG | | AGC | | TTA AGC | CTC AGC |
| | | | | TTG TCT | CTA TCT |
| | | | | TTG TCC | CTA TCC |
| | | | | TTG TCA | CTA TCA |
| | | | | TTG TCG | CTA TCG |
| | | | | TTG AGT | CTA AGT |
| | | | | TTG AGC | CTA AGC |
| | | | | CTT TCT | CTG TCT |
| | | | | CTT TCC | CTG TCC |
| | | | | CTT TCA | CTG TCA |
| | | | | CTT TCG | CTG TCG |
| | | | | CTT AGT | CTG AGT |
| | | | | CTT AGC | CTG AGC |

FIG.2

```
         LeuSer       SerArg
         TTATCT
         TTGTCT       TCTCGT
         CTTTCT       TCTCGC
         CTCTCT   X   TCTCGA   =   24
         CTATCT       TCTCGG
         CTGTCT

TTATCC       TCCCGT
         TTGTCC       TCCCGC
         CTTTCC       TCCCGA
         CTCTCC   X   TCCCGG   =   36
         CTATCC       TCCAGA
         CTGTCC       TCCAGG

TTATCA       TCACGC
         TTGTCA       TCACGT
         CTTTCA       TCACGA
         CTCTCA   X   TCACGG   =   36
         CTATCA       TCAAGA
         CTGTCA       TCAAGG

TTATCG       TCGCGT
         TTGTCG       TCGCGC
         CTTTCG       TCGCGA
         CTCTCG   X   TCGCGG   =   36
         CTATCG       TCGAGA
         CTGTCG       TCGAGG

AGTCGT
         CTCAGT   X   AGTCGC   =   4
                      AGTCGA
                      AGTCGG

AGCCGT
                      AGCCGC
                      AGCCGA
         CTCAGC   X   AGCCGG   =   6
                      AGCAGA
                      AGCAGG
```

FIG. 3

| LeuSer | | SerArg | |
|---|---|---|---|
| TTATCT | L,Y,I | TCTCGT | S,L,S |
| TTGTCT | L,C,V | TCTCGC | S,L,S |
| CTTTCT | L,F,F | TCTCGA | S,L,S |
| CTCTCT | L,S,L | TCTCGG | S,L,S |
| CTATCT | L,Y,I | | |
| CTGTCT | L,C,V | | |
| | | TCCCGT | S,P,P |
| TTATCC | L,Y,I | TCCCGC | S,P,P |
| TTGTCC | L,C,V | TCCCGA | S,P,P |
| CTTTCC | L,F,F | TCCCGG | S,P,P |
| CTCTCC | L,S,L | TCCAGA | S,P,Q |
| CTATCC | L,Y,I | TCCAGG | S,P,Q |
| CTGTCC | L,C,V | | |
| | | TCACGC | S,H,T |
| TTATCA | L,Y,I | TCACGT | S,H,T |
| TTGTCA | L,C,V | TCACGA | S,H,T |
| CTTTCA | L,F,F | TCACGG | S,H,T |
| CTCTCA | L,S,L | TCAAGA | S,Q,K |
| CTATCA | L,Y,I | TCAAGG | S,Q,K |
| CTGTCA | L,C,V | TCGCGT | S,R,A |
| | | TCGCGC | S,R,A |
| TTATCG | L,Y,I | TCGCGA | S,R,A |
| TTGTCG | L,C,V | TCGCGG | S,R,A |
| CTTTCG | L,F,F | TCGAGA | S,R,Q |
| CTCTCG | L,S,L | TCGAGG | S,R,Q |
| CTATCG | L,Y,I | | |
| CTGTCG | L,C,V | AGTCGT | S,V,S |
| | | AGTCGC | S,V,S |
| CTCAGT | L,S,R | AGTCGA | S,V,S |
| | | AGTCGG | S,V,S |
| CTCAGC | L,S,R | | |
| | | AGCCGT | S,G,P |
| | | AGCCGC | S,V,S |
| | | AGCCGA | S,V,S |
| | | AGCCGG | S,V,S |
| | | AGCAGA | S,A,Q |
| | | AGCAGG | S,A,Q |

FIG. 4

A 2amino to codon liblary(A is first)

A: GCTGCT,GCTGCC,GCTGCA,GCTGCG,GCCGCT,GCCGCC,GCCGCA,GCCGCG,
GCAGCT,GCAGCC,GCAGCA,GCAGCG,GCGGCT,GCGGCC,GCGGCA,GCGGCG

C: GCTTGT,GCTTGC,GCCTGT,GCCTGC,GCATGT,GCATGC,GCGTGT,GCGTGC

D: GCCGAT,GCCGAC,GCAGAT,GCAGAC,GCGGAT,GCGGAC

E: GCCGAA,GCCGAG,GCAGAA,GCAGAG,GCGGAA,GCGGAG

F: GCTTTT,GCTTTC,GCCTTT,GCCTTC,GCATTT,GCATTC,GCGTTT,GCGTTC

G: GCTGGT,GCTGGC,GCTGGA,GCTGGG,GCCGGT,GCCGGC,GCCGGA,GCCGGG,
GCAGGT,GCAGGC,GCAGGA, GCAGGG,GCGGGT,GCGGGC,GCGGGA,GCGGGG

H: GCTCAT,GCTCAC,GCCCAT,GCCCAC,GCACAT,GCACAC,GCGCAT,GCGCAC

I: GCTATT,GCTATC,GCTATA,GCCATT,GCCATC,GCCATA,GCAATT,GCAATC,
GCAATA,GCGATT,GCGATC,GCGATA

K: GCCAAA,GCCAAG,GCAAAA,GCAAAG,GCGAAA,GCGAAG

L: GCTTTA,GCTTTG,GCTCTT,GCTCTC,GCTCTA,GCTCTG,GCCTTA,GCCTTG,
GCCCTT,GCCCTC,GCCCTA,GCCCTG,GCATTA,GCATTG,GCACTT,GCACTC,
GCACTA,GCACTG,GCGTTA,GCGTTG,GCGCTT,GCGCTC,GCGCTA,GCGCTG

M: GCTATG,GCCATG,GCAATG,GCGATG

N: GCCAAT,GCCAAC,GCAAAT,GCAAAC,GCGAAT,GCGAAC

P: GCTCCT,GCTCCC,GCTCCA,GCTCCG,GCCCCT,GCCCCC,GCCCCA,GCCCCG,
GCACCT,GCACCC,GCACCA,GCACCG,GCGCCT,GCGCCC,GCGCCA,GCGCCG

Q: GCTCAA,GCTCAG,GCCCAA,GCCCAG,GCACAA,GCACAG,GCGCAA,GCGCAG

R: GCTCGT,GCTCGC,GCTCGA,GCTCGG,GCCCGT,GCCCGC,GCCCGA,GCCCGG,
GCCAGA,GCCAGG,GCACGT,GCACGC,GCACGA,GCACGG,GCAAGA,GCAAGG,
GCGCGT,GCGCGC,GCGCGA,GCGCGG,GCGAGA,GCGAGG

S: GCTTCT,GCTTCC,GCTTCA,GCTTCG,GCCTCT,GCCTCC,GCCTCA,GCCTCG,
GCCAGT,GCCAGC,GCATCT,GCATCC,GCATCA,GCATCG,GCAAGT,GCAAGC,
GCGTCT,GCGTCC,GCGTCA,GCGTCG,GCGAGT,GCGAGC

T: GCTACT,GCTACC,GCTACA,GCTACG,GCCACT,GCCACC,GCCACA,GCCACG,
GCAACT,GCAACC,GCAACA, GCAACG,GCGACT,GCGACC,GCGACA,GCGACG

V: GCTGTT,GCTGTC,GCTGTA,GCTGTG,GCCGTT,GCCGTC,GCCGTA,GCCGTG,
GCAGTT,GCAGTC,GCAGTA, GCAGTG,GCGGTT,GCGGTC,GCGGTA,GCGGTG

W: GCTTGG,GCCTGG,GCATGG,GCGTGG

Y: GCTTAT,GCTTAC,GCCTAT,GCCTAC,GCATAT,GCATAC,GCGTAT,GCGTAC

FIG. 6

| No | Amino acid | Number of patterns | No | Amino acid | Number of patterns |
|---|---|---|---|---|---|
| 1 | A | 4 | 11 | M | 1 |
| 2 | C | 2 | 12 | N | 2 |
| 3 | D | 2 | 13 | P | 4 |
| 4 | E | 2 | 14 | Q | 2 |
| 5 | F | 2 | 15 | R | 6 |
| 6 | G | 4 | 16 | S | 6 |
| 7 | H | 2 | 17 | T | 4 |
| 8 | I | 3 | 18 | V | 4 |
| 9 | K | 2 | 19 | W | 1 |
| 10 | L | 6 | 20 | Y | 2 |

FIG. 7

| No | Aminoacid | Codon | No | Aminoacid | Codon |
|---|---|---|---|---|---|
| 1 | A | GCT GCC GCA GCG | 11 | M | ATG |
| 2 | C | TGT TGC | 12 | N | AAT AAC |
| 3 | D | GAT GAC | 13 | P | CCT CCC CCA CCG |
| 4 | E | GAA GAG | 14 | Q | CAA CAG |
| 5 | F | TTT TTC | 15 | R | CGT CGC CGA CGG AGA AGG |
| 6 | G | GGT GGC GGA GGG | 16 | S | TCT TCC TCA TCG AGT AGC |
| 7 | H | CAT CAC | 17 | T | ACT ACC ACA ACG |
| 8 | I | ATT ATC ATA | 18 | V | GTT GTC GTA GTG |
| 9 | K | AAA AAG | 19 | W | TGG |
| 10 | L | TTA TTG CTT CTC CTA CTG | 20 | Y | TAT TAC |

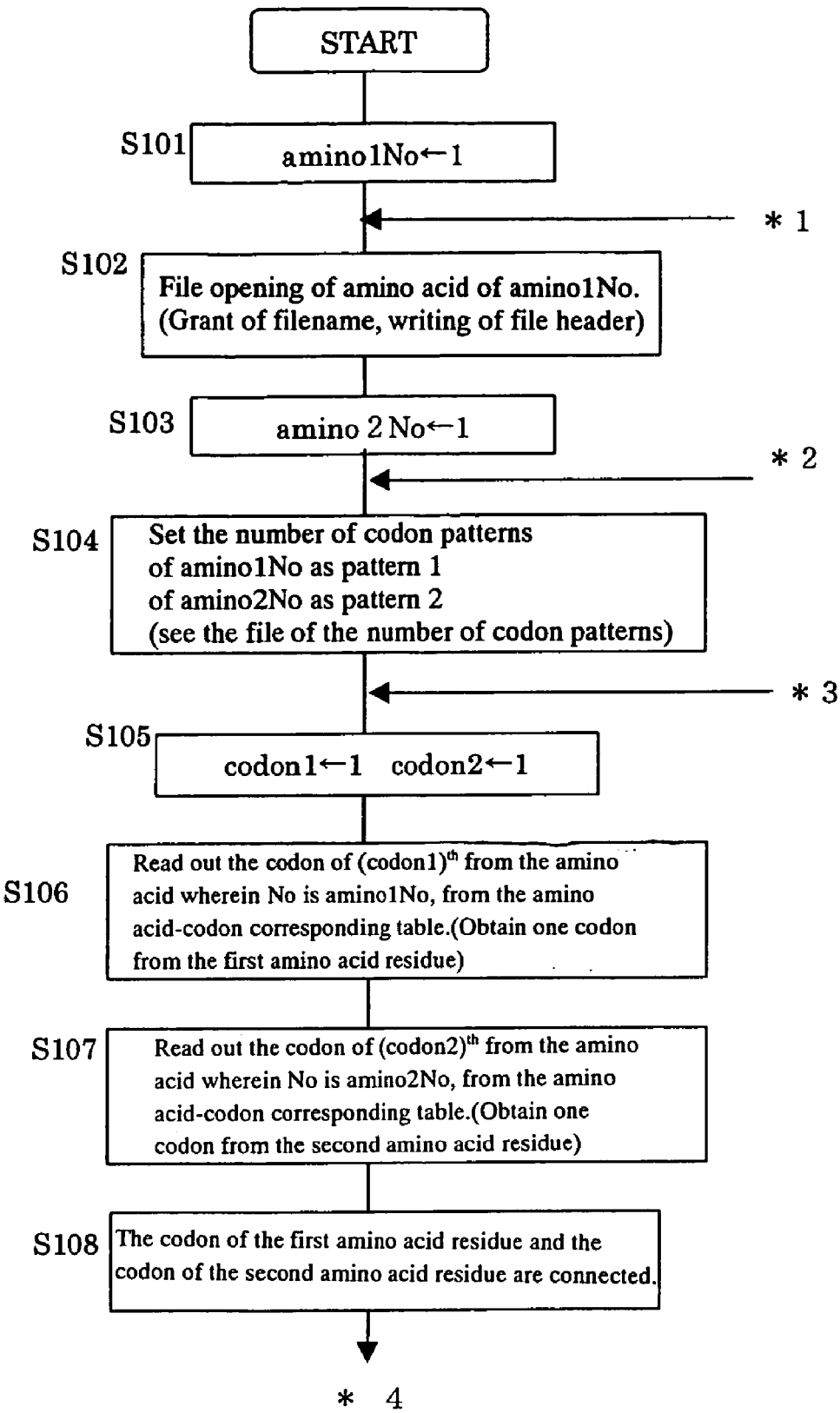

FIG. 10

Example of a file output) a case wherein the first amino acid residue of the above-mentioned (1) is "Y".

Filename: Yamino_to_codon.dat   File header

Y 2amino to codon library(Y is first)
A: TATGCT,TATGCC,TATGCA,TATGCG,TACGCT,TACGCC,TACGCA,TACGCG
C: TATTGT,TATTGC,TACTGT,TACTGC
D: TACGAT,TACGAC
E: TACGAA,TACGAG
F: TATTTT,TATTTC,TACTTT,TACTTC
G: TATGGT,TATGGC,TATGGA,TATGGG,TACGGT,TACGGC,TACGGA,TACGGG
H: TATCAT,TATCAC,TACCAT,TACCAC
I: TATATT,TATATC,TATATA,TACATT,TACATC,TACATA
K: TAGAAA,TAGAAG
L: TATTTA,TATTTG,TATCTT,TATCTC,TATCTA,TATCTG,TACTTA,TACTTG,TACCTT,TACCTC,TACCTA,TACCTG
M: TATATG,TACATG
N: *TACAAT,TACAAC*
P: TATCCT,TATCCC,TATCCA,TATCCG,TACCCT,TACCCC,TACCCA,TACCCG
Q: TATCAA,TATCAG,TACCAA,TACCAG
R: TATCGT,TATCGC,TATCGA,TATCGG,TACCGT,TACCGC,TACCGA,TACCGG,TACAGA,TACAGG
S: TATTCT,TATTCC,TATTCA,TATTCG,TACTCT,TACTCC,TACTCA,TACTCG,TACAGT,TACAGC
T: TATACT,TATACC,TATACA,TATACG,TACACT,TACACC,TACACA,TACACG
V: TATGTT,TATGTC,TATGTA,TATGTG,TACGTT,TACGTC,TACGTA,TACGTG
W: TATTGG,TACTGG
Y: TATTAT,TATTAC,TACTAT,TACTAC 20 kinds of amino acids (second residue)

a codon wherein the first residue "Y" and the second residue "*" are combined.

FIG. 11

| No | Amino acid | Codon-listing file | No | Amino acid | Codon-listing file |
|---|---|---|---|---|---|
| 1 | A | Aamino_to_codon.dat | 11 | M | Mamino_to_codon.dat |
| 2 | C | Camino_to_codon.dat | 12 | N | Namino_to_codon.dat |
| 3 | D | Damino_to_codon.dat | 13 | P | Pamino_to_codon.dat |
| 4 | E | Eamino_to_codon.dat | 14 | Q | Qamino_to_codon.dat |
| 5 | F | Famino_to_codon.dat | 15 | R | Ramino_to_codon.dat |
| 6 | G | Gamino_to_codon.dat | 16 | S | Samino_to_codon.dat |
| 7 | H | Hamino_to_codon.dat | 17 | T | Tamino_to_codon.dat |
| 8 | I | Iamino_to_codon.dat | 18 | V | Vamino_to_codon.dat |
| 9 | K | Kamino_to_codon.dat | 19 | W | Wamino_to_codon.dat |
| 10 | L | Lamino_to_codon.dat | 20 | Y | Yamino_to_codon.dat |

SEQUENCE LISTING

```
<160> NUMBER OF SEQ ID NOS: 3

<210> SEQ ID NO 1
<211> LENGTH: 26
<212> TYPE: PRT
<213> ORGANISM: Artificial Sequence
<220> FEATURE:
<223> OTHER INFORMATION: S1: Completely synthesized

<400> SEQUENCE: 1

Asn Gly Asn Asn Gly Asn Asn Gly Asn Asn Gly Asn Asn Gly Asn Asn
1               5                   10                  15

Gly Asn Gly Asn Asn Gly Asn Asn Gly Gly
            20                  25

<210> SEQ ID NO 2
<211> LENGTH: 15
<212> TYPE: PRT
<213> ORGANISM: Artificial Sequence
<220> FEATURE:
<223> OTHER INFORMATION: S2:Completely synthesized

<400> SEQUENCE: 2

Tyr Asn Gly Asp Asn Gly Asn Asn Gly Asp Asn Gly Asn Asn Gly
1               5                   10                  15

<210> SEQ ID NO 3
<211> LENGTH: 22
<212> TYPE: PRT
<213> ORGANISM: Artificial Sequence
<220> FEATURE:
<223> OTHER INFORMATION: S3: Completely synthesized

<400> SEQUENCE: 3

Asn Gly Asn Gly Asn Gly Asn Gly Asn Gly Leu Asn Tyr Leu Lys Ser
1               5                   10                  15

Leu Tyr Gly Gly Tyr Gly
            20
```

METHOD OF DESIGNING MULTIFUNCTIONAL BASE SEQUENCE

This application is a Continuation-in-part application of application Ser. No. 10/329,781, filed Dec. 27, 2002.

TECHNICAL FIELD

The present invention relates to the field of computational science for designing a multifunctional base sequence (a multifunctional microgene) which is associated with biological functions in a plurality of reading frames, and to the field of protein engineering for producing an artificial protein by using the multifunctional base sequence.

BACKGROUND ART

Knowledge concerning structures and functions of proteins obtained from genomic biology and post genomic biology can now be artificially reorganized on artificial proteins and actively utilized. As a method of rationally embedding a function on an artificial protein, a small base sequence (a microgene) is first designed to associate with a specific biological function, and then it is possible to reorganize the biological function on an artificial protein which is a translation product of a microgene polymer by polymerizing the microgene in a tandem manner (see Patent Document 1 and Non-Patent Document 1, for example), or by connecting plural microgenes (see Patent Document 2, for example). There is, for example, a method of microgene polymerization (see Patent Document 1 and Non-Patent Document 1, for example) to polymerize microgenes, which has an aspect that different translation reading frames of the microgenes are utilized in parallel. It is indispensable for the development of high-function artificial proteins to design and utilize a "multifunctional base sequence" which is embedded with a plurality of biological functions simultaneously in a plurality of reading frames, by taking advantage of this aspect of the microgene polymerization method (see Patent Document 3, for example).

To present, designing of such multifunctional base sequence underwent the process as follows: to set a given peptide sequence having a primary function as an initial value; to back-translate base by base to the base sequences according to a genetic code table; to create all base sequences capable of encoding the peptide sequence on the processor; then to write down a pool of peptide sequences which are encoded by all the base sequences created and which are arising from reading frames different from that of the first peptide sequence in the processor; and lastly to select peptides having the secondary and tertiary functions out of this pool of peptide sequences.

In this case, base sequences in which translation termination codons emerge in other reading frames at the junction points of residues in a peptide of the first reading frame also become objects of the calculation. Such base sequences accompanied with emergence of translation termination codons in other reading frames have to be excluded in the end from the standpoint of applicability of multifunctional genes. However, it was hard to exclude the base sequences in advance in a conventional algorithm as described above so that all the combinations had to be calculated, which required vast amount of calculation time. For example, there are approximately $687 \times 10^8$ variants of base sequences encoding the peptide sequence of NGNNGNNGNNGN-NGNNGNGNNGNNGG (SEQ ID NO: 4) in its first reading frame, and among them only about $4 \times 10^7$ variants are devoid of translation termination codons in the second and third reading frames. In the conventional method, however, all the variants of about $687 \times 10^8$ had to undergo calculation.

Patent Document 1
Japanese Laid-Open Patent Application No. 1997-322775
Patent Document 2
Japanese Laid-Open Patent Application No. 1997-154585
Patent Document 3
Japanese Laid-Open Patent Application No. 2001-352990
Non-Patent Document 1
Proc. Natl. Acad. Sci. USA 94, 3805-3810, 1997

The subject of the present invention is to provide a method of designing a multifunctional base sequence wherein the calculation time is largely shortened and the volume of memory consumption of a processor is largely reduced by calculating with the advance exclusion of base sequences which are accompanied with the emergence of translation termination codons in the second and third reading frames, and which should be excluded in the end.

The present inventors have made a keen study to solve the above described subject and focused on the fact that a dipeptide sequence (two amino acid residues) or a peptide sequence with longer length already contains information about translation products in the second and third reading frames. Then the present inventors have found that, when proteins are analyzed and calculated by regarding proteins as the duplicated and connective products of dipeptide sequences (two amino acid residues) or of short sequences with length longer than dipeptides, unlike in conventional methods where proteins are analyzed as connective products of 20 kinds of amino acids, the information can be analyzed in such a way as the information of translation products of the second and third reading frames is included within, and therefore the calculation time is largely shortened and the volume of memory consumption of a processor can be reduced to a great extent.

FIG. 1 shows an example of the course of processing to back-translate into base sequences by single amino acid units. For instance, there are six codons encoding leucine (Leu); TTA, TTG, CTT, CTC, CTA and CTG. There are also six codons encoding serine (Ser); TCT, TCC, TCA, TCG, AGT and AGC. To perform back translation for all base sequences that are capable of encoding a dipeptide "Leu-Ser", $6 \times 6 = 36$ variants of base sequences are first generated on the processor. Besides, for the case of the sequence "Leu-Ser-Arg" where arginine (Arg) is located on the third position, $36 \times 6 = 216$ variants of base sequences are generated on the processor. In this way, variants of base sequences corresponding to the total variants obtained by multiplying codons (1 to 6 variants) which have possibility for encoding the amino acid located at the $N^{th}$ position are generated on the processor, and then the processing moves on to the exclusion of base sequences containing translation termination codons (TAA, TAG, TGA) in other reading frames from among the base sequences. Since a base sequence containing a translation termination codon in other reading frames cannot be used as a multifunctional base sequence in the end, the exclusion of them at this stage will largely reduce the burden on the later calculation processing.

Next, a processing is considered under the recognition that a polypeptide sequence is a pool of 400 dipeptide variants and not a connection of 20 amino acid residues. When considering a base sequence which encodes a dipeptide, the first amino acid residue of the second and third reading frames in the base sequence are already defined in the first place. Therefore, it becomes possible to exclude in advance the sequences containing termination codons out of the pool of base sequences encoding a dipeptide. As shown in the aforementioned FIG. 1, there are eight sequences containing termination codons in the second reading frames and two sequences containing termination codons in the third reading frames among all 36 variants of base sequences capable of encoding the dipeptide "Leu-Ser". Therefore, it becomes possible to generate base sequences on the processor with the advance exclusion of termination codons by preparing 36−10=26 variants as codons corresponding to "Leu-Ser".

For example, when carrying out back-translation for a peptide comprising three residues of "Leu-Ser-Arg" and generating base sequences encoding the peptide on a processor, the sequence is processed as a sequence where two dipeptides, "Leu-Ser" and "Ser-Arg", are connected. Codons corresponding to "Leu-Ser" may thereafter be calculated for 6×6−10=26 variants as described above, and codons corresponding to "Ser-Arg" may be calculated for 6×6−4=32 variants (four variants contain termination codons in their second reading frames). Therefore, as shown in FIG. 2, it has become possible to obtain every base sequence with the length of 9-mer which encodes "Leu-Ser-Arg" in the first reading frame and not containing termination codons in the second and third reading frames by selecting and connecting the codon combinations, where serine is read by the same codon, from 26 variants of "Leu-Ser" 6-mer codons and from 32 variants of "Ser-Arg" 6-mer codons. As a result of this, (6×4)+(6×6)+(6×6)+(6×6)+(1×4)+(1×6)=142 variants would just be enough to be processed and calculated as shown in FIG. 2, whereas codon combinations according to the conventional methods required work of writing down sequences of 6×6×6=216 variants on a processor.

As described in the foregoing, an operation in which processing for the sequences which would finally be excluded due to the emergence of termination codons can be avoided by processing a polypeptide sequence as a pool of dipeptide units, preferably as a pool of sequential dipeptide units with duplicated amino acid residues, and by preparing a dipeptide-codon corresponding table (a corresponding table for nucleic acid sequences encoding dipeptides) where those having termination codons in the second and third reading frames are excluded in advance from codons of the dipeptide units. In fact, utilization of such algorithm enables the calculation time to be largely shortened as described later. Furthermore, it enables the necessary memory size to be also reduced to a great extent.

Besides, when a dipeptide-codon table, in which termination codons are excluded in advance, is translated in three reading frames, a sort of the first amino acids in the second and third reading frames are proved to be defined in the first place as FIG. 3 indicates. For example, the first reading frame TTA in the sequence of TTATCT for "Leu-Ser" is leucine (L), however, it is defined in the first place that the first amino acid in the second reading frame is tyrosine (Y) encoded by TAT, and the first amino acid in the third reading frame is isoleucine (I) encoded by ATC. Therefore, having given a dipeptide, thinkable sorts of amino acids in the second and third reading frames at that position are defined in the first place without back-translating to base sequences for each time. A considerable reduction in calculation processing can become possible by preparing in advance a "corresponding table for amino acids for each dipeptide-reading frame" to avoid the processing of back-translation to the base sequences. In this case, however, necessary information for connecting the first and the second dipeptide informations, as found in FIG. 2, is not included, and thus some extra information are needed for acquiring information about the possible "combinations". Nevertheless, sufficient amount of information can be yielded for finding out the sorts of amino acids that can be emerged in the second and third reading frames and for obtaining knowledge of their rough existing ratios when starting from a given peptide sequence in the first reading frame.

Information concerning the amino acid combinations which can be emerged in the second and third reading frames can also be given by further providing information of the kinds of codon used, for instance, to the aforementioned "corresponding table for amino acids for each dipeptide-reading frame". This turns out to be the same substance as the back-translation processing to the base sequences demonstrated in FIG. 2, yet it is characterized in that the volume of memory consumption can be reduced and the processing in which other information, such as information of the usage frequency of codons, is embedded can be performed.

The present invention has come to the completion based on the findings described above.

DISCLOSURE OF THE INVENTION

The present invention relates to: a method of designing a multifunctional base sequence wherein a base sequence has two or more functions in different reading frames of said base sequence, wherein a protein or a peptide encoded by a base sequence arising from one of the three reading frames is processed as a pool of oligopeptide units, and wherein the base sequence information of other reading frames contained in the oligopeptide sequence is utilized; the method of designing a multifunctional base sequence, wherein a corresponding table for nucleic acid sequences encoding oligopeptide sequences is produced and used; the method of designing a multifunctional base sequence, wherein a processing is carried out for a pool of sequential oligopeptide units having duplicated amino acid residues, and wherein a processing is carried out to connect oligopeptide units that have same codon for the duplicated amino acid residue in the sequential oligopeptide units; the method of designing a multifunctional base sequence, wherein a processing is carried out to connect amino acid residues encoded by base sequences of other reading frames contained in the oligopeptide units; the method of designing a multifunctional base sequence, wherein the processing for a pool of oligopeptide units is a processing to exclude base sequences containing termination codons from among the base sequences of other reading frames contained in the oligopeptide units; the method of designing a multifunctional base sequence, wherein the processing for a pool of oligopeptide units is a processing to select the whole or a part of a sequence of the interest from among the base sequences of other reading frames contained in the oligopeptide units; the method of designing a multifunctional base sequence, wherein the base sequence is a double-stranded base sequence; and the method of designing a multifunctional base sequence, wherein the oligopeptide units are dipeptide units or tripeptide units.

Further, the present invention relates to: a method for designing a base sequence wherein a base sequence that corresponds to a peptide sequence (a sequence of N amino acid residues) that was input on a computer is designed, comprising the following operations: a sequence corresponding table recorded with a pool of a codon pattern that can be obtained for every combination of two amino acid residues and does not contain a termination codon is set on a computer; said computer reads out a codon pattern of two amino acid residues from the $i^{th}$ (i is an integer from 1 to N−2) of a peptide sequence that was input and a codon pattern of two amino acid residues from the $(i+1)^{th}$ of said peptide sequence from the sequence corresponding table; it is determined whether the last three bases of the codon pattern of two amino acid residues at the $i^{th}$ of said peptide sequence and first three bases of two amino acid residues at the $(i+1)^{th}$ of said peptide sequence concord; if they concord, a processing of connecting said last three bases of the second codon pattern to the first codon pattern is executed until a base sequence that corresponds to N amino acid residues of the peptide sequence that was input is produced; and a base sequence that corresponds to peptide sequence is designed; a computer program which are executed in a computer, comprising: (A) a processing operation wherein input of a peptide sequence (a sequence of N amino acid residues) is accepted and (B) a processing operation wherein a codon pattern of two amino acid residues from the $i^{th}$ (i is an integer from 1 to N−2) of said peptide sequence that was input and a codon pattern of two amino acid residues from the $(i+1)^{th}$ of said peptide sequence are read out from a sequence corresponding table recorded with a pool of a codon pattern that can be obtained for every combination of two amino acid residues and does not contain a termination codon; it is determined whether the last three bases of the codon pattern of two amino acid residues at the $i^{th}$ of said peptide sequence and first three bases of two amino acid residues at the $(i+1)^{th}$ of said peptide sequence concord; if they concord, a processing of connecting said last three bases of the second codon pattern to the first codon pattern is executed until a base sequence that corresponds to N amino acid residues of the peptide sequence that was input is produced; are executed in the computer; a computer program which are executed in a computer, comprising: (A) an operation wherein input of a peptide sequence (a sequence of N amino acid residues) is accepted; (B) an operation wherein initial value 1 is set to variable i (i is an integer); (C) an operation wherein a sequence corresponding table recorded with a pool of a codon pattern that can be obtained for every combination of two amino acid residues and does not contain a termination codon is searched, one of the codon patterns that correspond to two amino acid residues from the $i^{th}$ of said peptide sequence that was input is selected and extracted, and then set as a first codon pattern; (D) an operation wherein said sequence corresponding table is searched, one of the codon patterns that correspond to two amino acid residues from the $(i+1)^{th}$ of said peptide sequence that was input is selected and extracted, and then set as a second codon pattern; (E) an operation wherein it is determined whether the last three bases of said first codon pattern and first three bases of said second codon pattern concord, and if they concord, the last three bases of said second codon pattern is connected to said first codon pattern, and then written down on a DNA sequence listing; (F) an operation conducted in a condition where variable i=1, wherein the processing of said operation C, operation D and operation E are executed to all combinations that are possible between the codon pattern that corresponds to two amino acid residues from the $i^{th}$ of said peptide sequence that was input that is recorded in said sequence corresponding table and the codon pattern that corresponds to two amino acid residues from the $(i+1)^{th}$ of said peptide sequence that was input that is recorded in said sequence corresponding table; (G) an operation wherein when said variable i is less than N−1, the value of variable i is advanced for one operation and proceeded to operation H, and if said variable i reaches N−1, the processing is finished; (H) an operation wherein one of the codon patterns is selected from said DNA sequence listing, and then set as said first codon pattern; (I) an operation wherein when variable i>1, the processing of said operation H, operation D and operation E are executed to all combinations that are possible between all the codon patterns of said recorded DNA sequence and the codon pattern that corresponds to two amino acid residues from the (i+1)th of said peptide sequence that was input that is recorded in said sequence corresponding table, and then proceeded to said operation G when the processing is completed; are executed in the computer; a computer program which are executed in a computer, comprising: (A) an operation wherein a codon pattern of a first amino acid residue is extracted from an amino acid-codon pattern corresponding table in which codon patterns that correspond to amino acid are set; (B) an operation wherein a codon pattern of a second amino acid residue is extracted from said amino acid-codon pattern corresponding table; (C) an operation wherein the codon pattern of said first amino acid residue and the codon pattern of said second amino acid residue are connected, the connected codon pattern is checked whether it contains a termination codon, if it does not contain a termination codon, a listing of codon patterns wherein the codon pattern of the first amino acid residue and the codon pattern of the second amino acid residue are connected is written down on a sequence corresponding table which shows the listing; (D) an operation wherein said operations A to C are executed for all combinations that are possible between a codon pattern that can be obtained by said first amino acid residue and a codon pattern that can be obtained by said second amino acid residue; (E) an operation wherein said operations A to D are executed for all combinations that are possible between the kinds of amino acids that can be obtained by said first amino acid residue and the kinds of amino acids that can be obtained by said second amino acid residue; are executed in the computer; a computer-readable recording medium that is recorded with a computer program which are executed in a computer, comprising: (A) a processing operation wherein input of a peptide sequence (a sequence of N amino acid residues) is accepted; and (B) a processing operation wherein a codon pattern of two amino acid residues from the $i^{th}$ (i is an integer from 1 to N−2) of said peptide sequence that was input and a codon pattern of two amino acid residues from the $(i+1)^{th}$ of said peptide sequence are read out from a sequence corresponding table recorded with a pool of a codon pattern that can be obtained for every combination of two amino acid residues and does not contain a termination codon; it is determined whether the last three bases of the codon pattern of two amino acid residues at the $i^{th}$ of said peptide sequence and first three bases of two amino acid residues at the $(i+1)^{th}$ of said peptide sequence concord; if they concord, a processing of connecting said last three bases of the second codon pattern to the first codon pattern is executed until a base sequence that corresponds to N amino acid residues of the peptide sequence that was input is produced.

Further, the present invention relates to a method for producing a multifunctional base sequence having more than two functions, wherein the method of designing a multifunctional base sequence, the computer program, or the recording medium is used; and a method for producing an artificial protein wherein the method for designing a multifunctional base sequence, the computer program, or the recording medium is used.

BRIEF DESCRIPTION OF DRAWINGS

FIG. 1 is an example of an algorithm for designing a base sequence encoding a dipeptide (Leu-Ser) which is devoid of termination codons in the second and third reading frames.

FIG. 2 is an example of an algorithm for designing a base sequence encoding a tripeptide (Leu-Ser-Arg) which is devoid of termination codons in the second and third reading frames.

FIG. 3 shows that a sort of the first amino acid in the second and third reading frames are defined in the first place by translating in three reading frames a dipeptide (Leu-Ser) codon table which is devoid of termination codons in the second and third reading frames.

FIG. 4 shows a codon table where the first amino acid of dipeptides is A (alanin) among the dipeptide-codon tables.

FIG. 6 shows an example of a number of codon patterns Table 13 of the present invention.

FIG. 7 shows an example of an amino acid-codon corresponding Table 14 of the present invention.

FIG. 8 is a flow chart (No. 1) that shows an embodiment of the production and processing of a codon-listing file of the present invention.

FIG. 10 shows an example of a codon-listing file (sequence corresponding table) 15 of the present invention.

FIG. 11 shows an example of a list wherein the amino acid and the codon-listing file of the present invention correspond.

BEST MODE OF CARRYING OUT THE INVENTION

Figure 5:
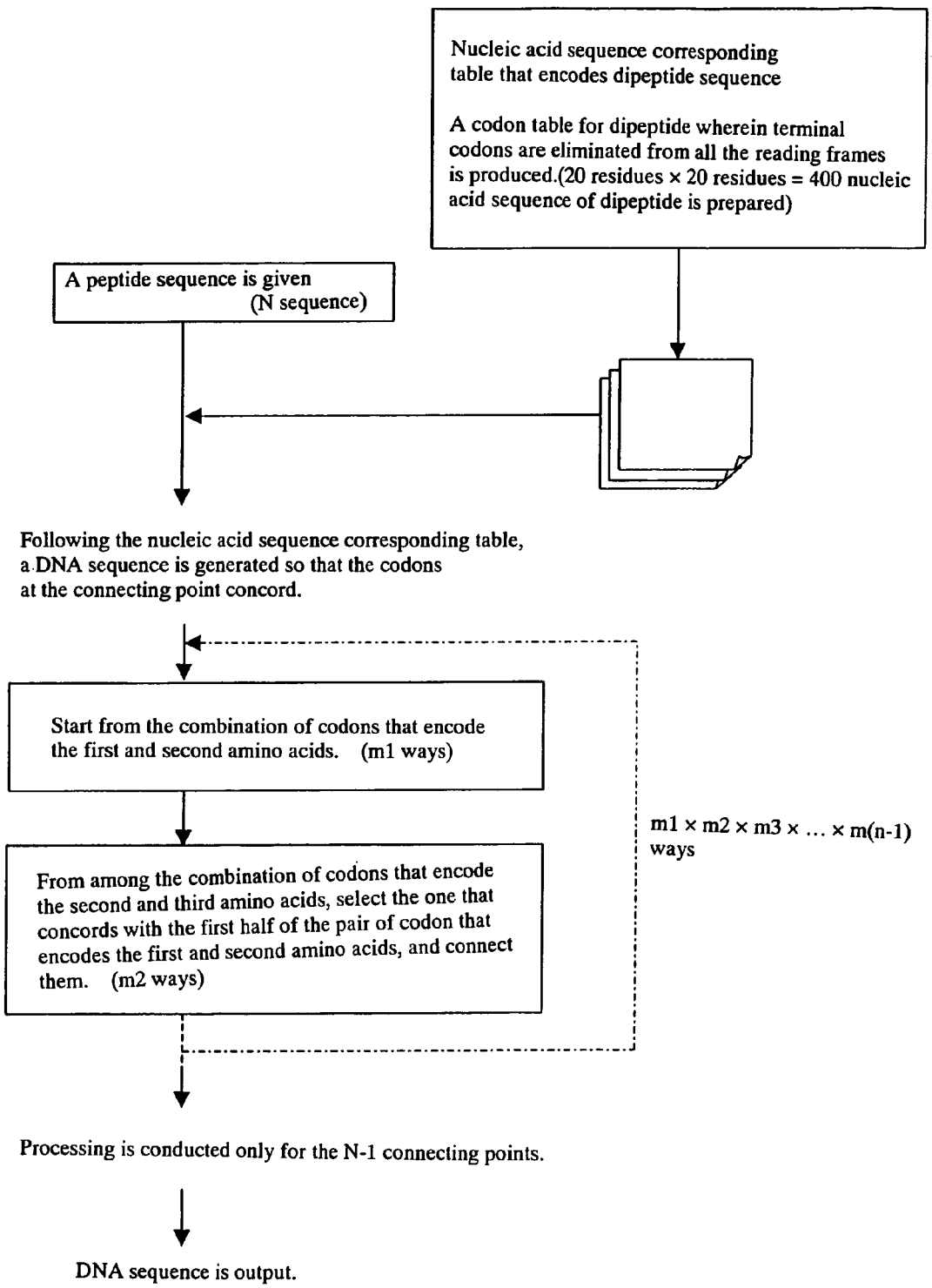
FIG. 5 shows a processing flow chart illustrating the method of designing a multifunctional base sequence of the present invention.
Figure 9:
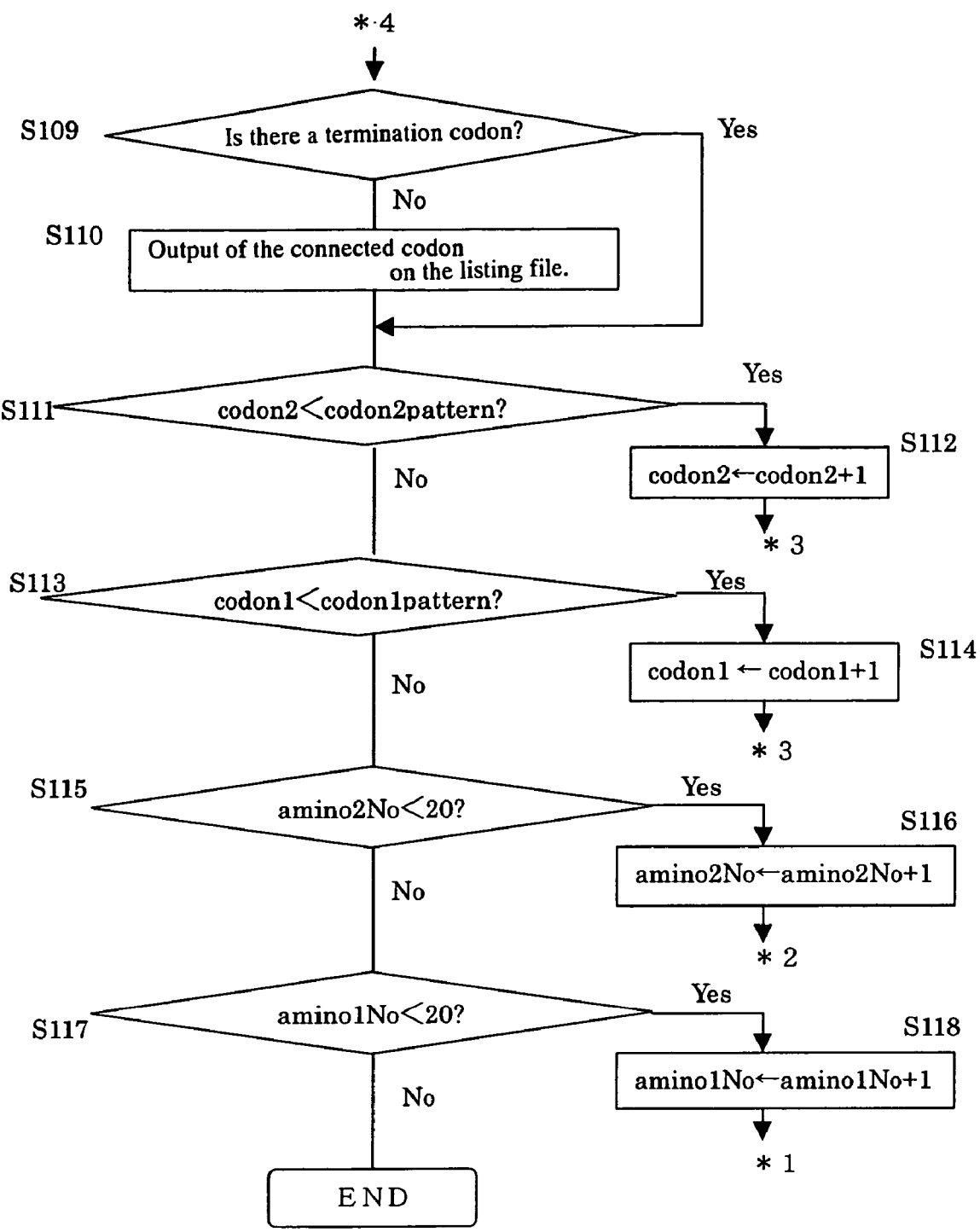
FIG. 9 is a flow chart (No. 2) that shows an embodiment of the production and processing of a codon-listing file of the present invention.

There is no particular limitation as to a method of designing a multifunctional base sequence of the present invention as long as it is a method of designing a multifunctional base sequence: wherein a base sequence has two or more functions in different reading frames of the base sequence; wherein proteins or peptides (usually, these proteins or peptides are given as translation products of the first reading frame), which are encoded by the base sequence deriving from one of three reading frames, are processed as a pool of oligopeptide units, preferably as a pool of dipeptide units; and wherein the base sequence information of other reading frames contained in oligopeptide sequences, preferably in dipeptide sequences, is utilized. However, it is preferable to produce in advance a corresponding table for nucleic acid sequences encoding oligopeptide sequences represented by a corresponding table for nucleic acid sequences encoding dipeptide sequences (a dipeptide-codon corresponding table), and to use the corresponding table. In this description, an oligopeptide means a peptide in which 2 to 8 amino acid residues are connected.

Combinations of dipeptide codons count 3721 ways which is the square of 64−3, among which 192 ways of combination are accompanied with the emergence of termination codons respectively in the second and third reading frames. This means 384/3721=10% plus can be excluded in advance from the calculation objects by constructing a dipeptide-codon corresponding table. For example, 10/36 in "Leu-Ser" and 4/36 in "Ser-Arg" will be excluded in advance from the calculation objects as described earlier. For instance, leucine-threonine "Leu-Thr" is exemplified to be a dipeptide sequence containing many combinations to be excluded from the calculation objects. Among 6×4=24 ways of codon combinations for "Leu-Thr", 16 combinations (TTA ACT; TTA ACC; TTA ACA; TTA ACG; TTG ACT; TTG ACC; TTG ACA; TTG ACG; CTAACT; CTAACC; CTAACA; CTAACG; CTGACT; CTGACC; CTGACA; CTGACG) are subjected to cancellation of calculation due to the termination codons, and calculation will be continued for 8 combinations (CTT ACT; CTT ACC; CTTACA; CTTACG; CTCACT; CTCACC; CTCACA; CTCACG), meaning that as much as ⅔ is excluded from the calculation objects in advance. Besides, in methionine-isoleucine "Met-Ile", all three kinds (ATGATT; ATGATC; ATGATA) come to possess a termination codon TGA in the second reading frame and are excluded from the calculation objects, therefore, calculation time can largely be shortened by checking in advance whether a given amino acid sequence for a protein or a peptide contains the "Met-Ile" dipeptide sequence.

Codon tables indicating the case where calculation is cancelled in the course of a program can be made the above-described dipeptide-codon corresponding table, however, it is usually sufficient to produce and prepare codon tables for 400 kinds indicating the case where calculation continues in the course of a program. Such codon tables may be, for example, produced for each of the first amino acids of dipeptides. Among dipeptide-codon tables, FIG. 4 displays 20 kinds of codon tables where the first amino acid of dipeptides is A (alanine), in the sequential order of AA, AC, AD, . . . , and so on.

In the method of designing a multifunctional base sequence of the present invention, it is preferable to carry out a processing for sequential oligopeptide units with duplicated amino acid residues, preferably for a pool of dipeptide units, and to perform a processing to connect dipeptide units having same codon for the duplicated amino acid residue in the sequential dipeptide units. Construction of an oligopeptide-codon corresponding table is enabled by the use of this algorithm. For example, as described earlier, when a peptide comprising three residues of "Leu-Ser-Arg" is back-translated and base sequences encoding the peptide are generated on the processor, the sequence is regarded as a sequence in which two dipeptides "Leu-Ser" and "Ser-Arg" are connected. Therefore, by connecting and processing the dipeptide units having the same codon for serine which is a duplicated amino acid residue, a codon corresponding table for tripeptide "Leu-Ser-Arg" can be produced and by using this codon corresponding table for the tripeptide "Leu-Ser-Arg", 74 variants are excluded and the objects for processing and calculation can be reduced to 142/216. Likewise, in the case of "Leu-Thr-Lys", the sequence is regarded as a connection of two dipeptides, "Leu-Thr" and "Thr-Lys", and dipeptide units having the same codon for threonine, a duplicated amino acid residue, are connected and processed to reduce the objects to 12/48. Furthermore, in the case of "Leu-Arg-Ser", the sequence is regarded as a connection of two dipeptides, "Leu-Arg" and "Arg-Ser", and dipeptide units having the same codon for arginine, a duplicated amino acid residue, are connected and processed to reduce the objects for processing and calculation to 144/216. Hence corresponding tables for oligopeptide units which are longer than tetrapeptide units can be constructed.

In the method of designing a multifunctional base sequence of the present invention, a processing can be carried out to connect amino acid residues which are encoded by base sequences of other reading frames contained in oligopeptide units, preferably in dipeptide units. Taking the dipeptide combination "Leu-Ser" (a case for LS) shown in FIG. 3 as an example, kinds of amino acids which can emerge in the second reading frame are C, F, S and Y when starting from a given peptide sequence of the first reading frame, whereas those which can emerge in the third reading frame are F, I, L, R and V. By utilizing the algorithm which employs such "corresponding table for amino acid sequence for each dipeptide-reading frame", approximate existing ratios of amino acid residues capable of emerging in the second or third reading frame can be acquired which are as follows: C;8 (8/26=0.31), F;4 (4/26=0.15), S;6 (6/26=0.23) and Y;8 (8/26=0.31) in the second reading frame, and F;4 (4/26=0.15), I; 8 (8/26=0.31), L;4 (4/26=0.15), R;2 (2/26=0.08) and V;8 (8/26=0.31) in the third reading frame.

Other than the processing to exclude base sequences including termination codons from the base sequences of other reading frames contained in oligopeptide units, preferably in dipeptide or tripeptide units, it is possible to carry out a processing to select base sequences containing the whole or a part of the sequence of the interest in the method of designing a multifunctional base sequence according to the present invention. Although the processing to select sequences of the interest is preferably carried out for the base sequences where termination codons have been excluded, it can also be carried out for the base sequences where termination codons have not been excluded. Such sequence of the interest is exemplified by a sequence with a function of the interest, and such function of the interest may roughly be grouped into: functions possessed by translation products of the whole or a part of the base sequence; and functions of the whole or a part of the base sequence per se.

The functions possessed by translation products as mentioned above include: function to easily form secondary structures such as α-helix-formation or the like; antigen function to induce neutralizing antibodies for such as virus or the like; function to activate immunity (Nature Medicine, 3: 1266-1270, 1997); function to promote or suppress cell proliferation; function to specifically recognize cancer cells; protein transduction function; cell-death-inducing function; function to present residues that determine antigens; metal-binding function; coenzyme-binding function; function to activate catalysts; function to activate fluorescence signal; function to bind to a specific receptor and to activate the receptor; function to bind to a specific factor involved in signal transduction and to modulate the action of the factor; function to specifically recognize biopolymers such as proteins, DNA, RNA, sugar or the like; cell adhesion function; function to localize proteins to the cell exterior; function to target at a specific intracellular organelle (mitochondrion, chloroplast, ER, etc.); function to be embedded in the cell membrane; function to form amyloid fibers; function to form fibrous proteins; function to form a protein gel; function to form a protein film; function to form a single molecular membrane; self-aggregation function; function to form particles; function to assist the formation of higher-order structure of other proteins; function to recognize inorganic crystals; function to suppress the growth of inorganic crystals; and the like. As for the functions of the base sequence per se as described above are exemplified by the followings: metal-binding function; coenzyme-binding function; function to activate catalysts; function to bind to a specific receptor and to activate the receptor; function to bind to a specific factor involved in signal transduction and to modulate the action of the factor; function to specifically recognize biopolymers such as proteins, DNA, RNA, sugar or the like; function to stabilize RNA; function to modulate the translation efficiency; function to suppress the expression of a specific gene; and so on.

There is no specific limitation as to a method of producing a multifunctional base sequence according to the present invention as long as it is a method of producing a multifunctional base sequence which comprises a process of selecting base sequences having two or more functions by using the method of designing a multifunctional base sequence of the present invention, and any base sequence having two or more functions in different reading frames of the base sequence can be an object of such multifunctional base sequence, where a base sequence is specifically exemplified by single- or double-stranded DNA or RNA sequences. These sequences can either take linear or cyclic structure, however, a sequence with linear structure is preferable because a polymerization method for a linear structured sequence has been established. Furthermore, it is preferable that the aforementioned multifunctional base sequence is devoid of termination codons in all three reading frames where the reading frames are shifted one-by-one within the base sequence, and especially for a double-stranded base sequence, it is preferable that all six reading frames in the base sequence are devoid of termination codons. Still further, such base sequence is particularly preferable that a termination codon will not emerge at the junction points (binding points) arising from the polymerization of the multifunctional base sequence.

The length of a multifunctional base sequence of the present invention will not be limited to a particular length. However, base sequences consisting of 15 to 500 bases or base pairs, particularly, 15 to 200 bases or base pairs, and more particularly, 15 to 100 bases or base pairs are preferable for a stable performance of DNA synthesis. Further, the following multifunctional base sequences may be used as a multifunctional base sequence of the present invention: a multifunctional base sequences which is modified for polymerization according to formation of random polymer of microgene (Publication of Japanese Laid-Open Patent Application No. 1997-154585) or the method of microgene polymerization (Publication of Japanese Laid-Open Patent Application No. 1997-322775) as described earlier, or by some other methods; and a multifunctional base sequence to which a natural base sequence is bound.

Base sequences having biological functions that are same as or different from the given functions can be selected by the computational science approach utilizing a computer. These approaches are exemplified more specifically by an approach in which selection is made using scores obtained by a biological function prediction program. Such biological function prediction program is exemplified by a program produced by statistically processing the correlations between biological functions of proteins and peptides and the primary structure of proteins and peptides. The potential for secondary structure formation of a peptide, for instance, can be assessed by using a previously reported protocol (Structure, Function, and Genetics 27: 36-46, 1997). By using this method, the possibility of α-helix- and β-strand-formation predicted at each residue position of the given peptide sequences is numerically displayed (larger values for higher possibility) The potential levels for α-helix- and β-strand-formation at all the residues of the given peptide sequences are totaled respectively and calculated as a probability of α-helix-formation of the given peptide and a probability of β-strand-formation of the given peptide, and then can be used for the assessment. Other than the above, the following programs are exemplified as function prediction programs: protein family data bases such as "Motiffind program" (Protein Sci., 5: 1991-1999, 1996) and the like for detecting the similarities to known motifs registered to, for example, "PROSITE" (Nucleic Acids Res., 27: 215-219, 1999); a similarity searching program "blast" for predicting functions based on the similarities to natural proteins (J. Mol. Biol., 215: 403-410, 1990); "SMART" program for calculating the similarities to various protein factors of the signal transduction system (Proc. Natl. Acad. Sci. USA, 95: 5857-5864, 1998); "PSORT" program for assessing the potential to localize proteins to the cell exterior or to intracellular organelles (Biochem. Sci., 24: 34-35, 1999); "SOSUI" program for assessing the potential to be embedded in the cell membrane (Bioinformatics, 4: 378-379, 1998); and so on.

Sequences obtained by binding two or more multifunctional base sequences of the different kinds with ligase or the like, or by binding a multifunctional base sequence to a natural base sequence with ligase or the like can be adopted as a multifunctional base sequence of the present invention. Further, a sequence obtained by separately producing the parts of the multifunctional sequence of the present invention and then binding these parts with ligase or the like can also be adopted as a multifunctional base sequence of the present invention. Still further, a sequence having two or more functions produced by the method of producing a multifunctional base sequence of the present invention as described above is also included in the multifunctional base sequence of the present invention.

There is no particular limitation as to a method of producing an artificial protein of the present invention as long as the method comprises: by using the method of designing a multifunctional base sequence of the present invention and from among all the combinations of base sequences encoding an amino acid sequence having a given function, selecting an artificial gene comprising a base sequence having a function same as or different from the aforementioned given function in the second and third reading frames which are different from that of the amino acid sequence having the aforementioned given function; and generating an artificial protein based on the sequence information of the artificial gene. However, the aforementioned biologic functions are preferable for a given function, and a biological function different from the given function is preferable in that diversity can be yielded. The above-mentioned amino acid sequence having a given function is covered by every amino acid sequence having a given function and will not be limited to a single amino acid sequence. For instance, if there are three amino acid sequences having a given function, a multifunctional base sequence will be selected out of all the combinations of base sequences encoding the three amino acid sequences. Other than the known sequences such as, for example, a sequence of the aforementioned neutralizing antigen for AIDS virus or a motif structure such as Glu-Leu-Arg or the like held by the α-chemokine which is a cytokine to leukemia, the following unknown sequences are exemplified as an amino acid sequence having such given function: a sequence arising from deletion, substitution or addition of one or more amino acids in the known sequences and having similar functions to those of the known sequences; a common sequence well preserved among organisms, which is involved in a specific biological function; and a sequence comprising an amino acid sequence avoided by an existing human protein, which has possibility of evading the surveillance of the human immune system.

The present invention will be explained in more detail below with reference to the examples. However, the scope of the invention will not be limited to these examples.

EXAMPLE 1

A primary sequence NGNNGNNGNNGNNGNNGNGN-NGNNGG (S1) (SEQ ID NO: S1) was given and among base sequences which encode this peptide sequence consisting of asparagine (N) and glycine (G), those not containing termination codons were generated on the processor according to the processing flow chart shown in FIG. 5. The number of total patterns of base sequences encoded in the first reading frame of this peptide sequence counts as much as $687 \times 10^8$ variants approx., and in conventional methods all of such base sequences were processed. However, by adopting the algorithm using the "nucleic acid sequence-dipeptide corresponding table" of the present invention, processing is only required for $4 \times 10^7$ variants approx. which do not contain translation termination codons in the second and third reading frames. As a result of this, the calculation time was shortened to about 15 minutes when the algorithm of the present invention was applied, in contrast to the fact that it took about two weeks for the calculation time in conventional methods. Owing to this, vain calculation processing which equals to about 99.95% of the total patterns can be avoided. A computer employing the specification of OS: Solaris2.7, CPU: Ultra SPARC-II was used for the calculation.

EXAMPLE 2

Similarly as in Example 1, a primary sequence YNGD-NGNNGDNGNNG (S2) (SEQ ID NO: S2) was given and DNA sequences encoding this peptide sequence were generated on the processor. The total patterns of base sequence variants encoded in the first reading frame were approximately $1 \times 10^6$. However, when the algorithm according to the "nucleic acid sequence-dipeptide corresponding table" of the present invention was applied, it was proved that the processing should only be carried out for about $1 \times 10^4$ variants that had no translation termination codons in the second and third reading frames.

EXAMPLE 3

In a similar manner as in Example 1, a primary sequence NGNGNGNGNGLNYLKSLYGGYG (S3) (SEQ ID NO: S3) was given and DNA sequences encoding this peptide sequences were generated. The total patterns of base sequence variants encoded in the first reading frame were approximately $87 \times 10^9$. However, when the algorithm according to the "nucleic acid sequence-dipeptide corresponding table" of the present invention was applied, it was proved that the processing should only be carried out for about $57 \times 10^7$ variants that had no translation termination codons in the second and third reading frames.

EXAMPLE 4

Furthermore, a specific example of a processing wherein base sequence is generated by a computer program will be explained, by using FIGS. 6 to 16.

1) A processing wherein a codon-listing file that corresponds to two amino acid residues is generated.

In the listing file, for every amino acid in the first residue, 20 files, which is the number of kinds of amino acids in each of the second residues, is produced (An example of the file is shown in FIG. 10. The content of this file will be hereinafter described). Therefore, 20 kinds of amino acid residues are combined on each two residues, and 400 ways of a combination from each two amino acids are produced. This processing will be explained by using FIGS. 8 to 11 and FIG. 15.

In the process of producing this codon-listing file, combinations that include termination codons are eliminated. Detailed description is as follows.

Figure 15:
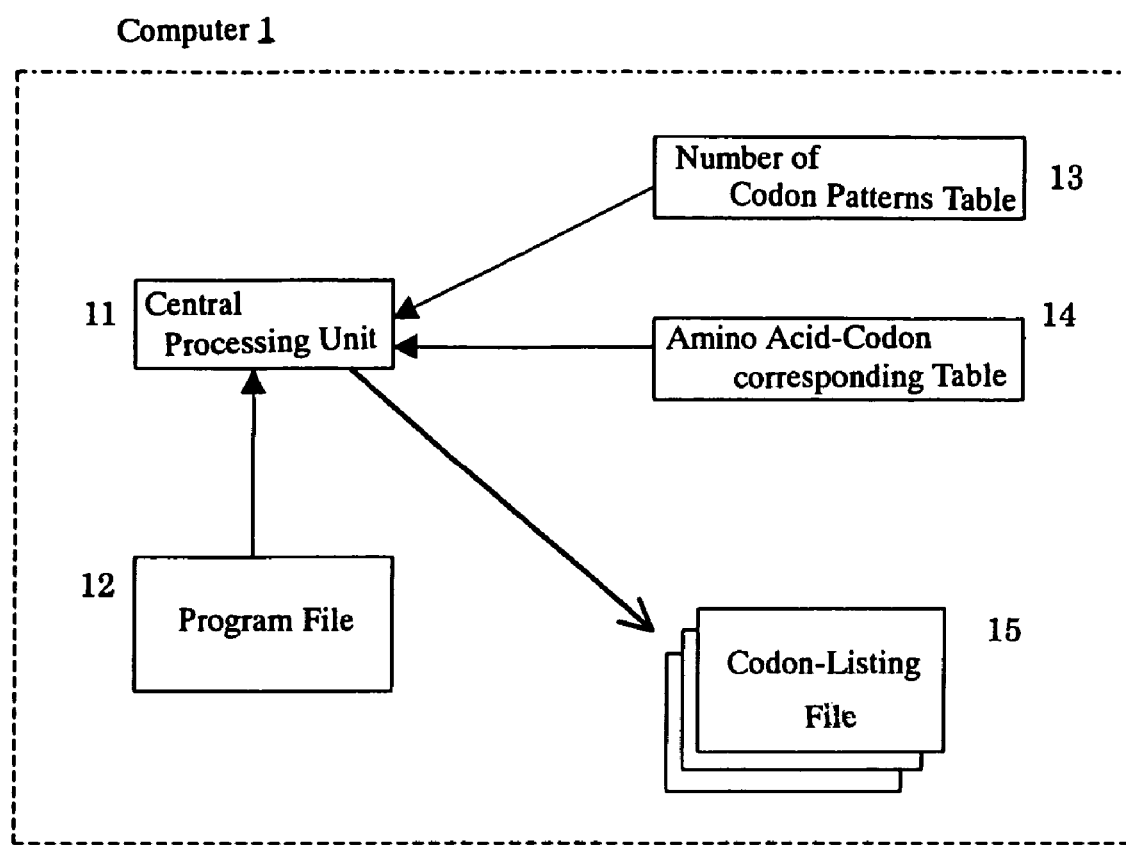
FIG. 15 is a block diagram that shows the configuration of a computer system, in an embodiment of a production and processing of a codon-listing file of the present invention.

As described in FIG. 15, a Number of Codon Patterns Table 13 and an Amino Acid-Codon Corresponding Table 14 are prepared on a Computer 1 that executes the processing of producing a listing file. After the preparation, the Central Processing Unit (CPU) 11 reads out a Program File 12 which is recorded with a processing program to be described hereinafter (FIGS. 8 and 9), and executes the processing program to produce Listing File 15.

This Program File 12 may be configured so that it is read out from a commutative recording medium by a drive device that is not shown in the figure, and is installed in Computer 1. As another embodiment, the program file may be configured in a manner where the network is connected to Computer 1 to download the program file.

A sequence number for each amino acid (No/in the explanation hereinafter, this sequence number (No) will be described as "amino acid number") is given in the Number of Codon Patterns Table 13 (see FIG. 6), and the number of codon patterns that exist in each of the amino acids is set correspondently. An amino acid number that common to the above-mentioned number of codon patterns table is given to the Amino Acid-Codon Corresponding Table 14 (see FIG. 7), and codons that correspond to each of the amino acids are stored.

In the present embodiment, the number of codon patterns table and the amino acid-codon corresponding table are presented as independent tables. However, a table where both of these are combined (a table wherein the number of patterns and the codon sequence are corresponded according to the name of amino acid and the amino acid number) may also be prepared.

Next, these tables are used to produce codon-listing files for every 20 kinds of amino acids. The processing for producing said file (the processing executed by the Program File 3 mentioned above) will be explained by using the flowcharts of FIGS. 8 and 9.

(S101) The variable amino1No showing the first amino acid residue that produces a codon-listing file is substituted with an initial value 1.

(S102) A codon-listing file regarding an amino acid wherein the amino acid number is the first aminoNo is opened. In the present embodiment, the file is named "name of the first amino acid residue+amino_to_codon.dat". In addition, a file header, "name of the first amino acid residue+2 amino to codon library (name of the first amino acid residue+is first)" is entered to this codon-listing file.

The example shown in FIG. 10 is a codon-listing file wherein the first amino acid residue is "Y", and therefore, the filename is "Yamino_to_codon.dat" and the file header is "Y 2 amino to codon library (Y is first)".

(S103) The variable amino2No showing the amino acid number of the second amino acid residue that is the subject to be connected, is substituted with an initial value 1.

(S104) Variable pattern 1 and pattern 2 are substituted with the number of codon patterns of the amino acid number aminoNo1 in the first amino acid residue and that of the amino acid number aminoNo2 in the second amino acid residue that are read out from the number of codon patterns table, respectively.

When the first amino acid residue is "Y" (in this case, the amino1No is not set at initial value 1, but at 20) and the second amino acid residue is "A" (amino2No is 1), value 2 is set for pattern 1, and value 4 is set for pattern 2.

(S105) Variable codon 1, which is the order of the codon stored in the amino acid-codon corresponding table of the first amino acid residue, and variable codon 2, which is the order of the codon stored in the amino acid-codon corresponding table of the second amino acid residue, are substituted with initial value 1, respectively.

(S106) The codon at the first codon, which is in the record of the amino acid wherein the amino acid number is amino1No, is read out from the amino acid-codon corresponding table. One codon at the first amino acid residue is obtained thereby.

In the case where one amino acid residue is "Y", "TAT" is read out if codon 1 is 1, and "TAC" is read out if it is 2.

(S107) The codon at the second codon, which is in the record of the amino acid wherein the amino acid number is amino2No, is read out from the amino acid-codon corresponding table. One codon at the second amino acid residue is obtained thereby.

In the case where the second amino acid residue is "A", "GCT" is read out if codon 2 is 1.

(S108) The codon at the first amino acid residue and the codon at the second amino acid residue obtained from S106 and S107 described above, are combined.

(S109) It is examined whether termination codons "TAA", "TAG" and "TGA" are included in the codon combined in S107 mentioned above. For example, when the codon combined in S108 is "TATAAT", S110 mentioned below will not be executed because termination codon "TAA" is included.

(S110) The combined codons wherein termination codons were not included in S109 mentioned above are written down in the codon-listing file.

The example in FIG. 10 shows that the first amino acid residue is "Y" and the second amino acid residue is "A". When a combined codon "TATGCT" is produced in S110 mentioned above, a combined codon "TATGCT" is written down in the record wherein this second residue is "A".

(S111, S112) It is checked whether variable codon 2 is smaller than pattern 2. In the case where codon 2 is smaller than pattern 2, codon 2 is advanced for one step and the processing of S105 to S110 mentioned above are executed. This is done in order to conduct the processing of reading out the next codon from the record of the second amino acid residue in the amino acid-codon table, and then connecting it.

In the case where codon 2 is not smaller than pattern 2 (or becomes the same), it means that the processing of reading out all the codons from the record of the second amino acid residue and writing them down in the codon-lising file is completed. Therefore, it is proceeded to S113.

(S113, S114) It is checked whether variable codon 1 is smaller than pattern 1. In the case where codon 1 is smaller than pattern 1, codon 1 is advanced for one step and the processing of S105 to S112 mentioned above are executed. This is done in order to conduct the processing of reading out the next codon from the record of the first amino acid residue in the amino acid-codon table, and then connecting it.

In the case where codon 1 is not smaller than pattern 1 (or becomes the same), it means that the processing of reading out all the codons from the record of the first amino acid residue and writing them down in the codon-lising file is completed. Therefore, it is proceeded to S115.

(S115, S116) It is checked whether variable amino2No is smaller than 20. In the case where amino2No is smaller than 20, aminoNo2 is advanced for one step and the processing of S104 to S114 mentioned above are executed. This is done in order to produce a record of the next second amino acid residue during the process wherein the first amino acid residue produces a codon-listing file of the amino acid of aminoNo1.

In the example of FIG. 10, aminoNo2 is advanced for one step from 1 to 2, when the combined codons wherein the second amino acid residue are "A" are all read out, and therefore, it is proceeded to the processing of producing a record regarding amino acid "C" wherein the amino acid number is 2.

(S117, S118) It is checked whether variable amino1No is smaller than 20. In the case where amino1No is smaller than 20, aminoNo2 is advanced for one step and the processing of S102 to S116 mentioned above are executed. This is done in order to produce a codon-listing file of the next first amino acid residue, since the first amino acid residue has completed producing the codon-listing file of the amino acid of aminoNo1.

In this way, a codon-listing file like the one shown in FIG. 10 is produced for every amino acid. A list wherein the amino acid and the codon-listing file correspond is shown in FIG. 11. Since there are 20 kinds of amino acids, 20 files are produced.

2) Processing of generating total DNA sequence from the peptide sequence that was input.

The processing (computer program) of generating a total DNA sequence from the peptide sequence wherein input is done, by using the codon-listing file produced in the processing of 1 mentioned above, will be explained by using FIGS. 12 to 14 and FIG. 16.

A sequence corresponding table recorded with a pool of a codon pattern wherein the codon pattern can be obtained according to each combination of the two amino acid residues and does not include a termination codon, is set up on a computer. The codon pattern of the two amino acid residues from the $i^{th}$ (i is an integer from 1 to N−2) of the peptide sequence that was input (the N of the sequence of amino acid residue), and the codon pattern of the two amino acid residues from the $(i+1)^{th}$ of said peptide sequence are read out from the aforementioned sequence corresponding table. Then, it is determined whether the three bases from the end of the codon pattern of the $i^{st}$ of the two amino acid residues of the aforementioned peptide sequence and the first three bases of the $(i+1)^{th}$ of two amino acid residues of the aforementioned peptide sequence concord. If they concord, processing of connecting the last three bases of the aforementioned second codon pattern with the aforementioned first codon pattern, is executed until a base sequence that corresponds to the N of amino residue of the peptide sequence that was input is produced, and a base sequence that corresponds to the peptide sequence is designed.

The processing mentioned above will be explained further in details hereinafter.

Figure 16:
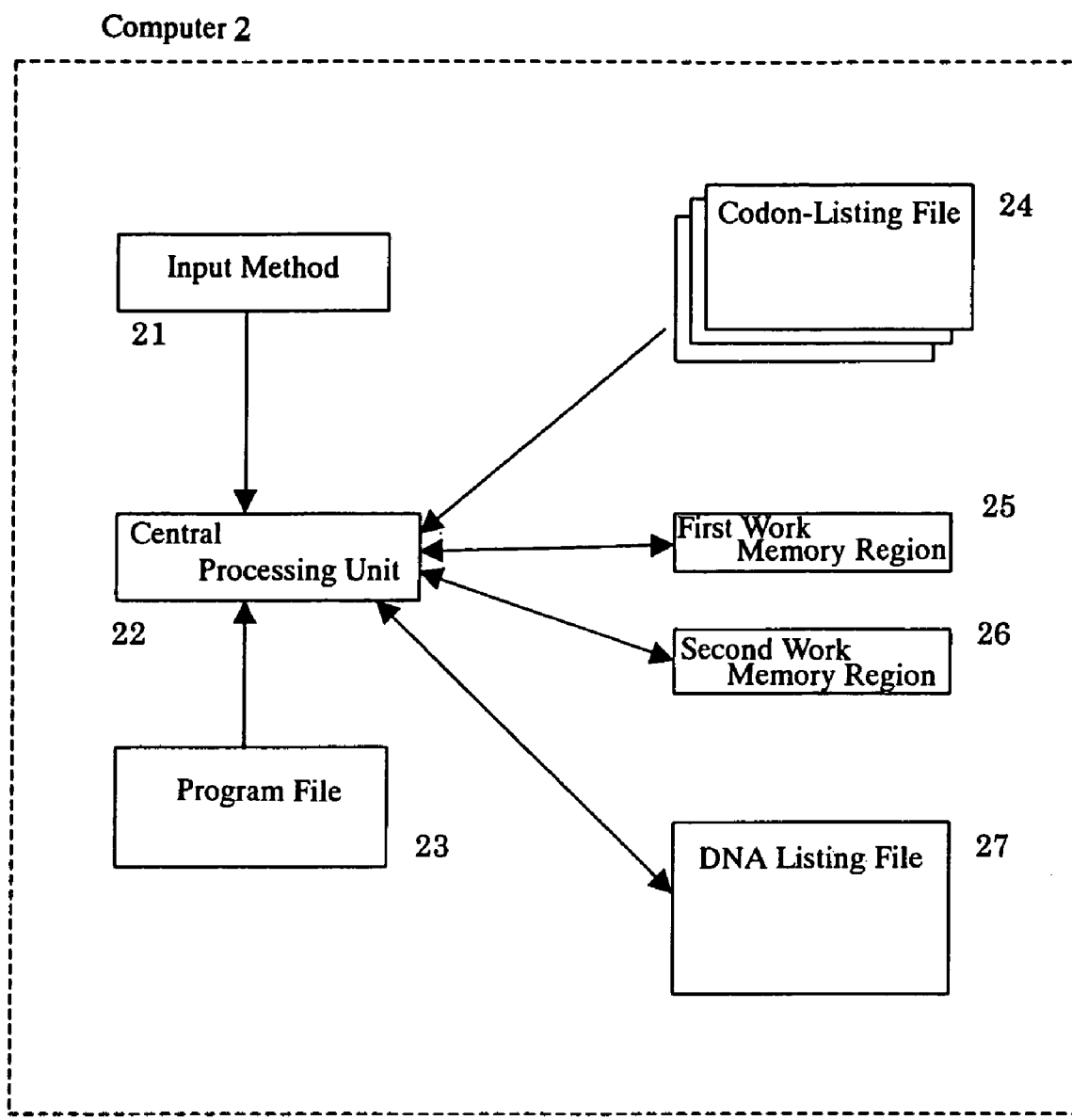
FIG. 16 is a block diagram that shows the configuration of a computer system, in an embodiment of a processing wherein total DNA sequence is generated from the peptide sequence that was input of the present invention.

As shown in FIG. 16, a Listing File 24 is prepared on Computer 2 which has an Input Method 21, then, the Central Processing Unit 22 reads out a Program File 23 which is recorded with a processing program described hereinafter (disclosed in FIGS. 12 and 13), and the processing program is executed to produce a Listing File 27. During this process, a First Work Memory Region 25 and a Second Work Memory Region 26 are secured on the computer memory.

The same computer as that of the computer that executes the processing of producing a listing file mentioned above, can be used for this Computer 11. In such a case, the same file as that of the Listing File 4 in FIG. 15 is used for Listing File 15.

Further, it may be configured to incorporate the (other) listing files that had already been produced into Computer 11.

The Program File 23 may be configured so that it is read out from a commutative recording medium by a drive device that is not shown in the figure, and is installed in Computer 2. As another embodiment, the program file may be configured in a manner where the network is connected to Computer 2 to download the program file.

Figure 12:
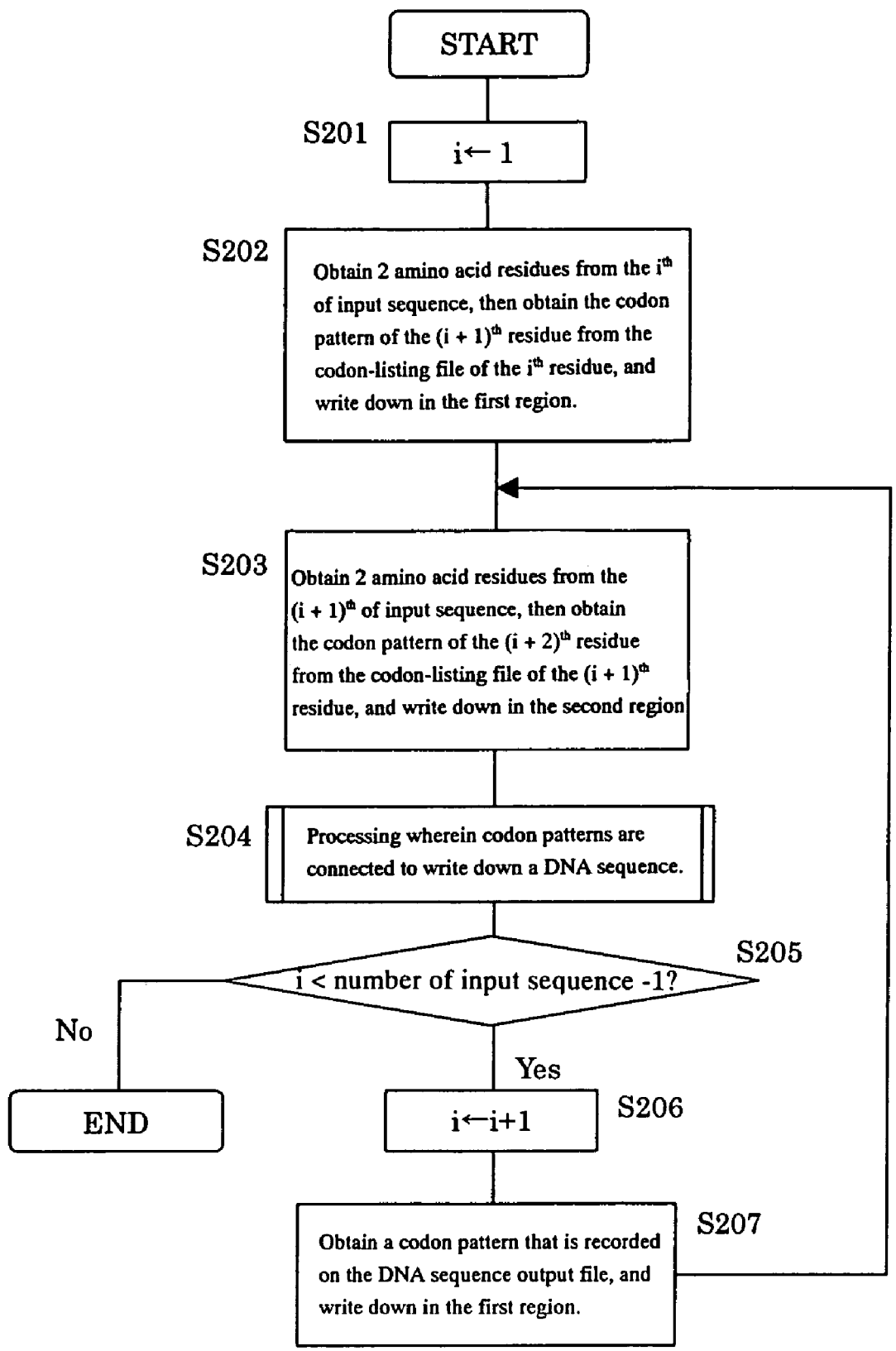
FIG. 12 is a flow chart (No. 1) that shows an embodiment of a processing wherein total DNA sequence is generated from the peptide sequence that was input of the present invention.
Figure 13:
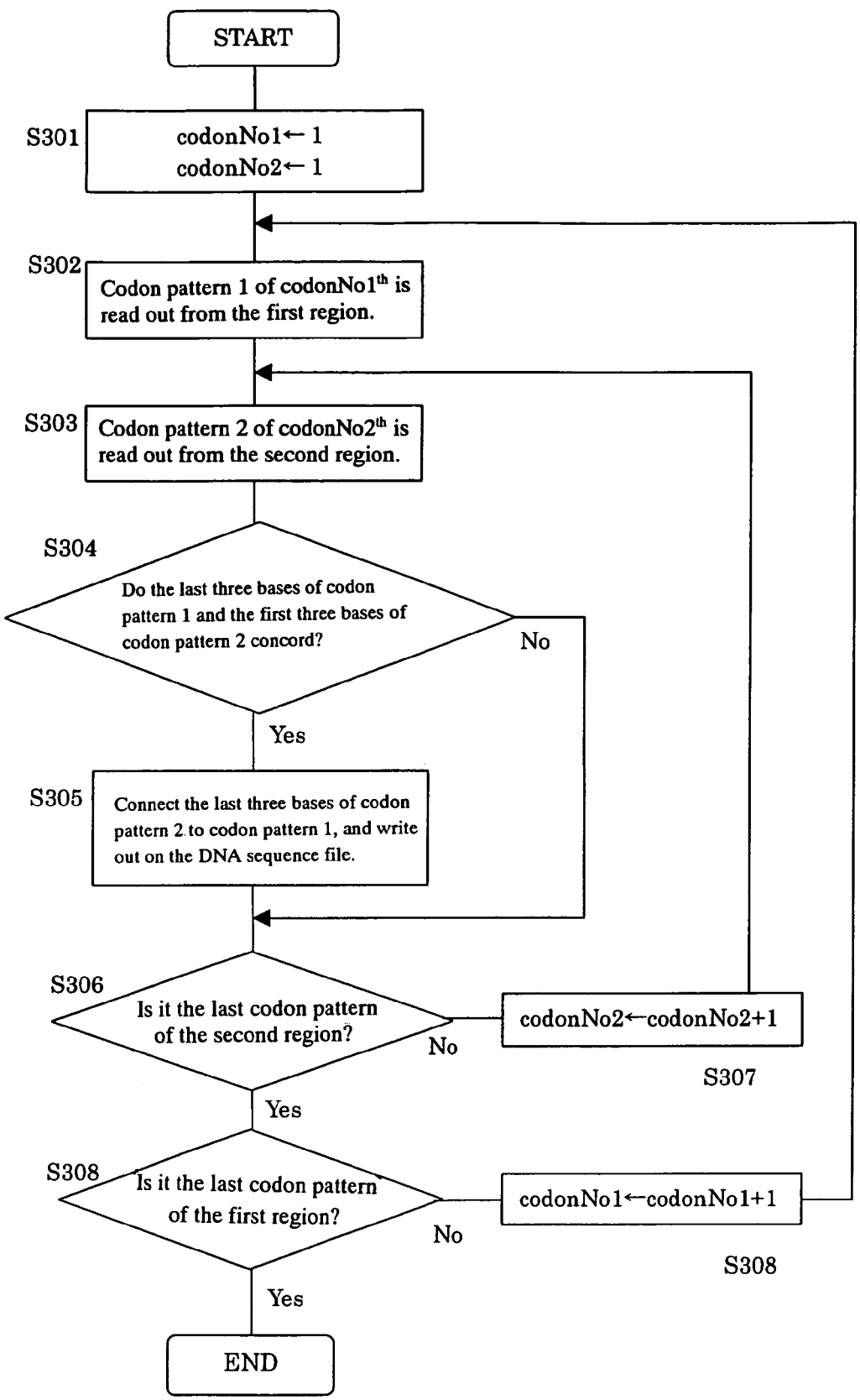
FIG. 13 is a flow chart (No. 2) that shows an embodiment of a processing wherein total DNA sequence is generated from the peptide sequence that was input of the present invention.
Figure 14:
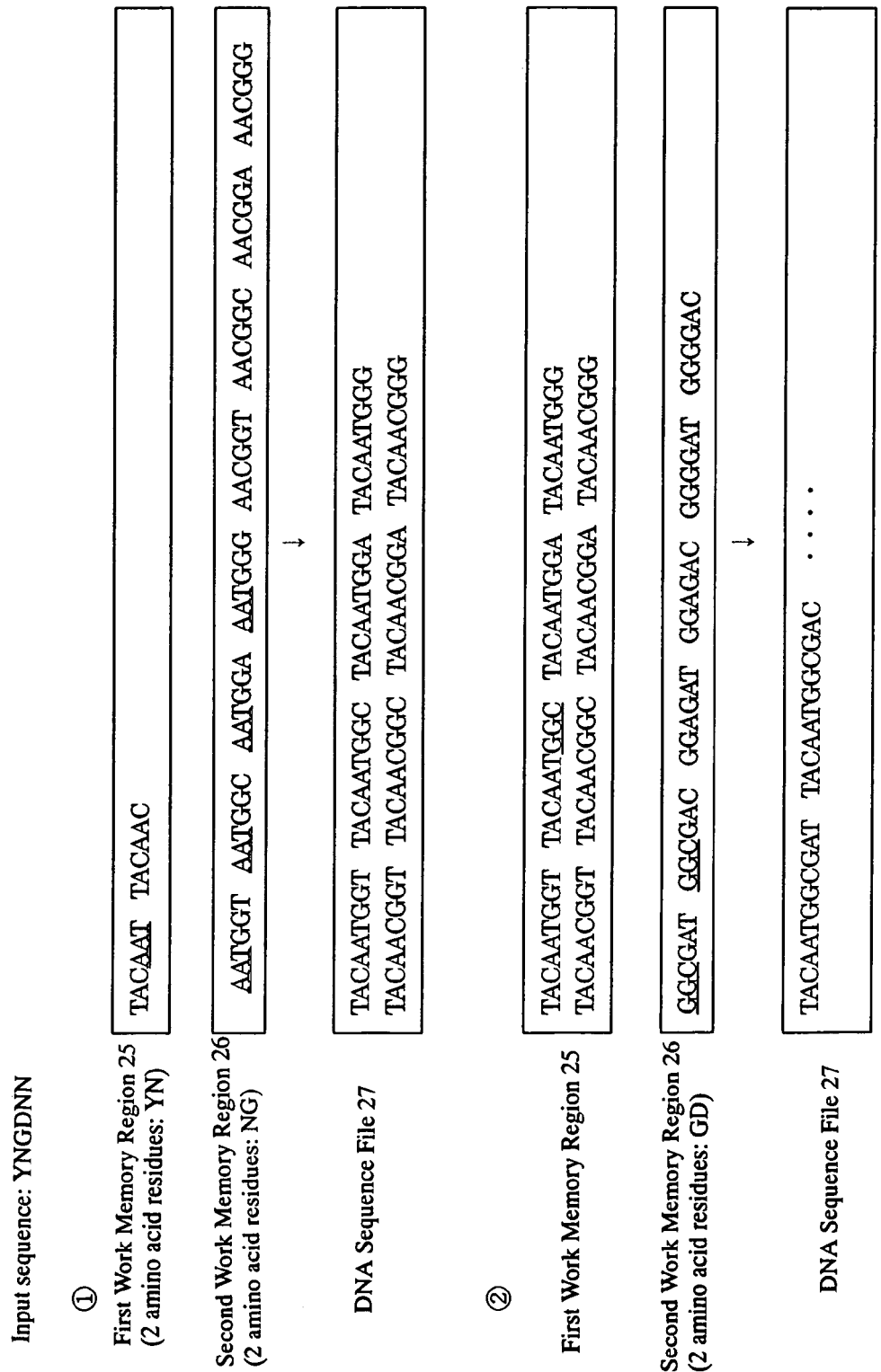
FIG. 14 shows an example of a flow of the processing of the present invention wherein, for input sequence: YNGDNN, (1) a First Work Memory Region 25 depicts TACAAT (SEQ ID NO: 5) and TACAAC (SEQ ID NO: 6); A Second Work Memory Region 26 depicts AATGGT (SEQ ID NO: 7). AATGGC (SEQ ID NO: 8), AATGGA (SEQ ID NO: 9), AATGGG (SEQ ID NO: 10), AACGGT(SEQ ID NO: 11), AACGGC (SEQ ID NO: 12), AACGGA (SEQ ID NO: 13) AND AACGGG (SEQ ID NO: 14); a DNA Sequence File 27 depicts TACAATGGT (SEQ ID NO: 15), TACAATGGC (SEQ ID NO: 16), TACAATGGA (SEQ ID NO: 17), TACAATGGG (SEQ ID NO: 18), TACAACGGT (SEQ ID NO: 19), TACAACGGC (SEQ ID NO: 20), TACAACGGC (SEQ ID NO: 21), TACAACGGG (SEQ ID NO: 22), (2) a First Memory Region 25 depicts TACAATGGT (SEQ ID NO: 23), TACAATGGC (SEQ ID NO: 24), TACAATGGA (SEQ ID NO: 25); TACAATGGG (SEQ ID NO: 26), TACAACGGT (SEQ ID NO: 27), TACAACGGC (SEQ ID NO: 28), TACAACGGA (SEQ ID NO: 29) and TACAACGGG (SEQ ID NO: 30), Second Work Memory Region 26 depicts GGCGAT (SEQ ID NO: 31), GGCGAC (SEQ ID NO: 32), GGAGAT (SEQ ID NO: 33), GGAGAC (SEQ ID NO: 34), GGGGAT (SEQ ID NO: 35), and GGGGAC (SEQ ID NO: 36), and DNA Sequence File 27 depicts TACAATGGCGAT (SEQ ID NO: 37) and TACAATGGCGAC (SEQ ID NO: 38).

FIGS. 12 and 13 are flow charts that show the processing of the present embodiment, and FIG. 14 is an example of a flow chart explaining the flow of processing in the case where the input sequence is "YNGDNN".

(S201) First, variable 1 is substituted with an initial value 1.

(S202) Two amino acid residues from the $i^{th}$ of the input sequence is obtained, the codon pattern of the $(i+1)^{th}$ residue is obtained from the codon-listing file of the $i^{th}$ residue, and are written down in the first work memory region (Note that in the flow chart of FIGS. 12 and 13, the first work memory region and the second work memory region are abbreviated as first region and second region, respectively).

Explaining from the example in FIG. 14, when i is initial value 1, the first amino acid residue is "Y". Therefore, "TACAAT" and "TACAAC", which are codon patterns wherein the second amino acid residue is "N", are read out from the codon-listing file "Yamino_to_codon.dat" (see FIG. 11), then written down in the first work memory region (FIG. 14 (1)).

(S203) Two amino acid residues from the $(i+1)^{th}$ of the input sequence are obtained, and the codon pattern of the $(i+2)^{th}$ residue is obtained from the codon-listing file of the $(i+1)^{th}$ residue, then written down in the second work memory region.

In the example (1) shown in FIG. 14, it is amino acid $(i+_1)^{th}$ residue when i is an initial value 1, that is, the second amino acid residue is "N". Therefore, all of the eight codon patterns such as "AATGGT", which is a codon pattern wherein the third amino acid residue is "G", are read out from the codon-listing file "Namino_to_codon.dat" (it is omitted in the figure, however, as described above, also in the case of amino acid "N", a codon-listing file that is the same as in the case of amino acid "Y" as described in FIG. 11, is produced), then written down in the second work memory region.

(S204) The codon patterns written down in the first work memory region and the second work memory region are connected to conduct the processing of writing down a DNA sequence on a DNA sequence file. Details regarding this processing will be explained later with the use of FIG. 13.

(S205) It is determined whether variable i reached the input sequence number −1. The example in FIG. 14 shows that the input sequence length is 6, therefore, the processing is finished, since it means that the processing of connecting the codon pattern to the sixth amino acid "N" which is the input sequence length, is finished when i reaches 5, and the DNA sequence that has already been written down on the output file becomes the final DNA sequence.

(S206) When variable i has not reached the input sequence number −1, i is advanced for one step.

(S207) Further, a codon pattern recorded on a DNA sequence file is obtained, and is written down on a first work memory region.

In the present embodiment, all the codon patterns recorded on the DNA sequence file are written down on the first work memory region. However, since the memory region expands as the number of codon pattern that was output in the sequence file increases, it may be constructed so that the codon patterns are written down one by one.

Further, the processing of S204 mentioned above will be explained by using FIG. 13.

(S301) The variable codonNo1 and codonNo2 are substituted with an initial value 1, respectively.

(S302) The codon pattern of the first of codonNo (this will be called codon pattern 1) is read out from the first work memory region.

In the example of FIG. 14 (1), TACAAT is read out first.

(S303) The codon pattern 2 of the second of codonNo (this will be called codon pattern 2) is read out from the second work memory region.

In the example of FIG. 14 (1), AATGGT is read out first.

(S304) The last three bases of codon pattern 1 that was read out in S302 mentioned above, and the first three bases of codon pattern 2 are read out.

(S305) If concordance is found in S304 mentioned above, the last three bases of codon pattern 2 is connected to codon pattern 1, and is written down on a DNA sequence file.

According to the example of the first processing in FIG. 14 (1) decribed above, codon pattern 1 is "TACAAT" and codon pattern 2 is "AATGGT", therefore, the last three bases of the former and the first three bases of the latter are both "AAT" (indicated in the figure with underline), which concords. Consequently, "TACAATGGT", which is a combination of the last three bases "GGT" of codon pattern 2 with codon pattern 1 "TACAAT" is obtained, and is written down on a DNA sequence file.

(S306, S307) It is determined whether the codon pattern of the codonNo2 of the second work memory region that is presently processed is the final pattern of the second work memory region (compare the number of codon patterns of the variable codon No 2 and the second work memory region), otherwise, advance codonNo2 for one step, and execute the processing of S303 to S305 mentioned above. If it is final, then proceed to S308.

In the example mentioned above, the codon pattern 1 "TACAAT" of the first work memory region and the codon pattern "AATGGT" of the second work memory region are connected, then "AATGGC" is read out as codon pattern 2, followed by the processing of determining whether codon pattern 2 can be connected to codon pattern 1 "TACAAT". In this case, "AAT" can also be connected, and therefore, a codon pattern "TACAATGGC" can be obtained. In this way, codon pattern 2 that is pointed by a variable codon No 2 from the second work memory region is read out to determine whether it can be connected to codon pattern 1 "TACAAT". If it can be connected, the processing of writing down on a DNA sequence file is executed. When the codon pattern 2 processes until "AATCCC", which is the final codon pattern of the second work memory region, it means that the processing of connecting it to codon pattern 1 "TACAAT" is completed.

(S308, 309) It is determined whether the codon pattern of the codonNo1 of the first work memory region that is presently processed is the final pattern of the first work memory region (compare the number of codon patterns of the variable codonNo1 and the first work memory region), otherwise, advance codonNo1 for one step, and execute the processing of S303 to S305 mentioned above. If it is final, then the processing is finished.

In the example mentioned above, if the processing is finished until "AACGGG", which is the final codon pattern 2 of the second work memory region, then the next codon pattern 1 "TACAAC" is read out from the first work memory region, and it is determined whether it can be connected to the codon pattern in the second work memory region. If it can be connected, the processing of writing down on a DNA sequence file is executed.

The example of FIG. 14 (1) mentioned above explains the processing when i is 1, that is, when the two sets of two amino acid residues YN and NG are connected. For the DNA sequence produced in this processing, a processing of connecting it with the two amino acid residues GD is executed.

Here is a brief description of this processing. Since it is determined that the connection to all of the input sequences in S205 of FIG. 12 is not completed, i is advanced for one step in S206. Further, as shown in FIG. 14 (2), the content of DNA Sequence File 27 is set in the First Work Memory 25, the codon pattern of the two amino acid residues GD is set in the Second Work Memory 26, the DNA sequence is connected by the logic shown in FIG. 13, and then written down on DNA Sequence File 27.

Such processing is executed until all the connections of the input sequence YNGDNN is completed.

The DNA sequence (base sequence) recorded on the DNA sequence file can be output by output means (display and printer, for example) that is not indicated in the figure, by the control of Computer 2.

The embodiment mentioned above conducts a processing wherein the base sequence to be connected is first written down on the First Work Memory 25 and the Second Work Memory 26, however, it is not limited to this method. For example, it may be configured so that the two amino acid residues to be connected are read out directly from the codon-listing file (Counting of the order of reading out is conducted in the same manner as that of the embodiment mentioned above). Further, the DNA sequence (that is still in the process of generating) that is written down in the DNA Listing File 27, is processed by being first written down in the First Work Memory 25 at S207, however, in the case where it is i>2 or more in S302 mentioned above, this processing of writing down is not conducted, and it may be configured to read out the codon pattern 2 directly from the DNA Sequence File 27.

INDUSTRIAL APPLICABILITY

The present invention makes it possible to design a multifunctional base sequence where the calculation time is largely shortened and the volume of memory consumption of a processor is largely reduced by calculating in a way that the base sequences are excluded in advance which are accompanied with the emergence of translation termination codons, which are to be excluded finally, in the second and third reading frames. The present invention also makes it possible to analyze translation products in the second and third reading frames without once back-translating peptide sequences to base sequences, and therefore, calculation speed of the algorithm which analyzes the property of peptides encoded by the same base sequence in different reading frames can largely be reduced and the memory consumption can be saved.

The invention claimed is:

1. A method of designing a multifunctional base sequence wherein a base sequence has two or more functions in different reading frames of said base sequence, wherein sequence data of a protein or a peptide encoded by a base sequence arising from one of the three reading frames is processed as a pool of oligopeptide units, wherein the base sequence information arising from other reading frames contained in the oligopeptide sequence is utilized, wherein a result of the method is outputted to a display, a memory, or another computer on a network, and wherein the processing for the pool of oligopeptide units is a processing to exclude base sequences containing termination codons from among the base sequences of other reading frames contained in the oligopeptide units.

2. The method of designing a multifunctional base sequence according to claim 1, wherein a corresponding table for nucleic acid sequences encoding oligopeptide sequences is produced and used.

3. The method of designing a multifunctional base sequence according to claim 1, wherein a processing is carried out for a pool of sequential oligopeptide units having duplicated amino acid residues, and wherein a processing is carried out to connect oligopeptide units that have the same codon for the duplicated amino acid residue in the sequential oligopeptide units.

4. The method of designing a multifunctional base sequence according to claim 1, wherein a processing is carried out to connect amino acid residues encoded by base sequences of other reading frames contained in the oligopeptide units.

5. The method of designing a multifunctional base sequence according to claim 1, wherein the processing for a pool of oligopeptide units is a processing to select the whole or a part of a sequence of interest from among the base sequences of other reading frames contained in the oligopeptide units.

6. The method of designing a multifunctional base sequence according to claim 1, wherein the base sequence is a double-stranded base sequence.

7. The method of designing a multifunctional base sequence according to claim 1, wherein the oligopeptide units are dipeptide units or tripeptide units.

8. A method for designing a base sequence wherein a base sequence that corresponds to a peptide sequence (a sequence of N amino acid residues) that was input on a computer is designed, comprising the following operations: a sequence corresponding table recorded with a pool of a codon pattern that can be obtained for every combination of two amino acid residues and does not contain a termination codon is set on a computer; said computer reads out a codon pattern of two amino acid residues from the $i^{th}$ (i is an integer from 1 to N−2) of a peptide sequence that was input and a codon pattern of two amino acid residues from the $(i+1)^{th}$ of said peptide sequence from the sequence corresponding table; it is determined whether the last three bases of the codon pattern of two amino acid residues at the $i^{th}$ of said peptide sequence and first three bases of two amino acid residues at the $(i+1)^{th}$ of said peptide sequence concord; if they concord, a processing of connecting said last three bases of the second codon pattern to the first codon pattern is executed until a base sequence that corresponds to N amino acid residues of the peptide sequence that was input is produced; and a base sequence that corresponds to peptide sequence is designed and is output to a display, printer, memory or another computer on a network.

9. A computer program which is executed in a computer, wherein the computer program is embodied on a computer readable medium, comprising: (A) a processing operation wherein input of a peptide sequence (a sequence of N amino acid residues) is accepted and (B) a processing operation wherein a codon pattern of two amino acid residues from the $i^{th}$ (i is an integer from 1 to N−2) of said peptide sequence that was input and a codon pattern of two amino acid residues from the $(i+1)^{th}$ of said peptide sequence are read out from a sequence corresponding table recorded with a pool of a codon pattern that can be obtained for every combination of two amino acid residues and does not contain a termination codon; it is determined whether the last three bases of the codon pattern of two amino acid residues at the $i^{th}$ of said peptide sequence and first three bases of two amino acid residues at the $(i+1)^{th}$ of said peptide sequence concord; if they concord, a processing of connecting said last three bases of the second codon pattern to the first codon pattern is executed until a base sequence that corresponds to N amino acid residues of the peptide sequence that was input is produced and is output to a display, printer, memory or another computer on a network; are executed in the computer.

10. A computer program which is executed in a computer, wherein the computer program is embodied on a computer readable medium, comprising: (A) an operation wherein input of a peptide sequence (a sequence of N amino acid residues) is accepted; (B) an operation wherein initial value 1 is set to variable i (i is an integer); (C) an operation wherein a sequence corresponding table recorded with a pool of a codon pattern that can be obtained for every combination of two amino acid residues and does not contain a termination codon is searched, one of the codon patterns that correspond to two amino acid residues from the $i^{th}$ of said peptide sequence that was input is selected and extracted, and then set as a first codon pattern; (D) an operation wherein said sequence corresponding table is searched, one of the codon patterns that correspond to two amino acid residues from the $(i+1)^{th}$ of said peptide sequence that was input is selected and extracted, and then set as a second codon pattern; (E) an operation wherein it is determined whether the last three bases of said first codon pattern and first three bases of said second codon pattern concord, and if they concord, the last three bases of said second codon pattern is connected to said first codon pattern, and then written down on a DNA sequence listing; (F) an operation conducted in a condition where variable i=1, wherein the processing of said operation C, operation D and operation E are executed to all combinations that are possible between the codon pattern that corresponds to two amino acid residues from the $i^{th}$ of said peptide sequence that was input that is recorded in said sequence corresponding table and the codon pattern that corresponds to two amino acid residues from the $(i+1)^{th}$ of said peptide sequence that was input that is recorded in said sequence corresponding table; (G) an operation wherein when said variable i is less than N−1, the value of variable i is advanced for one operation and proceeded to operation H, and if said variable i reaches N−1, the processing is finished; (H) an operation wherein one of the codon patterns is selected from said DNA sequence listing, and then set as said first codon pattern; (I) an operation wherein when variable i>1, the processing of said operation H, operation D and operation E are executed to all combinations that are possible between all the codon patterns of said recorded DNA sequence and the codon pattern that corresponds to two amino acid residues from the $(i+1)^{th}$ of said peptide sequence that was input that is recorded in said sequence corresponding table, and then proceeded to said operation G when the processing is completed; are executed in the computer, and wherein a result of the method is outputted to a display, a memory, or another computer on a network.

11. A computer program which is executed in a computer, wherein the computer program is embodied on a computer readable medium, comprising: (A) an operation wherein a codon pattern of a first amino acid residue is extracted from an amino acid-codon pattern corresponding table in which codon patterns that correspond to amino acid are set; (B) an operation wherein a codon pattern of a second amino acid residue is extracted from said amino acid-codon pattern corresponding table; (C) an operation wherein the codon pattern of said first amino acid residue and the codon pattern of said second amino acid residue are connected, the connected codon pattern is checked whether it contains a termination codon, if it does not contain a termination codon, a listing of codon patterns wherein the codon pattern of the first amino acid residue and the codon pattern of the second amino acid residue are connected is written down on a sequence corresponding table which shows the listing; (D) an operation wherein said operations A to C are executed for all combinations that are possible between a codon pattern that can be obtained by said first amino acid residue and a codon pattern that can be obtained by said second amino acid residue; (E) an operation wherein said operations A to D are executed for all combinations that are possible between the kinds of amino acids that can be obtained by said first amino acid residue and the kinds of amino acids that can be obtained by said second amino acid residue; are executed in the computer, and wherein a result is outputted to a display, a memory, or another computer on a network.

12. A computer-readable recording medium that is recorded with a computer program which is executed in a computer, comprising: (A) a processing operation wherein input of a peptide sequence (a sequence of N amino acid residues) is accepted; and (B) a processing operation wherein a codon pattern of two amino acid residues from the $i^{th}$ (i is an integer from 1 to N−2) of said peptide sequence that was input and a codon pattern of two amino acid residues from the $(i+1)^{th}$ of said peptide sequence are read out from a sequence corresponding table recorded with a pool of a codon pattern that can be obtained for every combination of two amino acid residues and does not contain a termination codon; it is determined whether the last three bases of the codon pattern of two amino acid residues at the $i^{th}$ of said peptide sequence and first three bases of two amino acid residues at the $(i+1)^{th}$ of said peptide sequence concord; if they concord, a processing of connecting said last three bases of the second codon pattern to the first codon pattern is executed until a base sequence that corresponds to N amino acid residues of the peptide sequence that was input is produced, and wherein a result of the method is outputted to a display, a memory, or another computer on a network.

13. A method for producing a multifunctional base sequence having more than two functions, comprising:
designing the multifunctional base sequence wherein a base sequence has two or more functions in different reading frames of said base sequence, wherein a protein or a peptide encoded by a base sequence arising from one of the three reading frames is processed as a pool of oligopeptide units, and wherein the base sequence information arising from other reading frames contained in the oligopeptide sequence is utilized, wherein the processing for the pool of oligopeptide units is a processing to exclude base sequences containing termination codons from among the base sequences of other reading frames contained in the oligopeptide units; and
producing the multifunctional base sequence, as designed, wherein the multifunctional base sequence is output to a display, printer, memory or another computer on a network.

14. A method for producing an artificial protein, comprising:
designing a multifunctional base sequence wherein a base sequence has two or more functions in different reading frames of said base sequence, wherein a protein or a peptide encoded by a base sequence arising from one of the three reading frames is processed as a pool of oligopeptide units, wherein the base sequence information arising from other reading frames contained in the oligopeptide sequence is utilized, wherein the processing for the pool of oligopeptide units is a processing to exclude base sequences containing termination codons from among the base sequences of other reading frames contained in the oligopeptide units; and
producing the artificial protein data from the multifunctional base sequence and outputting to a display, printer, memory or another computer on a network.

15. The method of designing a multifunctional base sequence according to claim 2, wherein a processing is carried out for a pool of sequential oligopeptide units having duplicated amino acid residues, and wherein a processing is carried out to connect oligopeptide units that have the same codon for the duplicated amino acid residue in the sequential oligopeptide units.

16. The method of designing a multifunctional base sequence according to claim 2, wherein a processing is carried out to connect amino acid residues encoded by base sequences of other reading frames contained in the oligopeptide units.

17. The method of designing a multifunctional base sequence according to claim 16, wherein the processing for a pool of oligopeptide units is a processing to exclude base sequences containing termination codons from among the base sequences of other reading frames contained in the oligopeptide units.

18. The method of designing a multifunctional base sequence according to claim 16, wherein the processing for a pool of oligopeptide units is a processing to select the whole or a part of a sequence of the interest from among the base sequences of other reading frames contained in the oligopeptide units.

19. The method of designing a multifunctional base sequence according to claim 18, wherein the base sequence is a double-stranded base sequence.

20. The method of designing a multifunctional base sequence according to claim 19, wherein the oligopeptide units are dipeptide units or tripeptide units.

* * * * *